United States Patent [19]
Bundle et al.

[11] Patent Number: 5,962,423
[45] Date of Patent: Oct. 5, 1999

[54] TREATMENT OF BACTERIAL DYSENTERY

[75] Inventors: David R. Bundle; Pavel Kitov; Randy J. Read; Hong Ling; Glen Armstrong, all of Edmonton, Canada

[73] Assignee: The Governors of the University of Alberta, Alberta, Canada

[21] Appl. No.: 09/130,495

[22] Filed: Aug. 7, 1998

[51] Int. Cl.[6] .......................... A61K 31/70; A61K 31/74; A61K 31/745; A61K 31/785
[52] U.S. Cl. ................................. 514/25; 424/DIG. 16; 514/53; 514/61
[58] Field of Search ...................... 424/DIG. 16; 514/25, 514/53, 61

[56] References Cited

U.S. PATENT DOCUMENTS

| | | | |
|---|---|---|---|
| 4,137,401 | 1/1979 | Lemieux et al. | 536/116 |
| 4,238,473 | 12/1980 | Lemieux et al. | 536/1.11 |
| 4,362,720 | 12/1982 | Lemieux et al. | 514/25 |
| 5,041,516 | 8/1991 | Fréchet et al. | 528/44 |
| 5,079,353 | 1/1992 | Ratcliffe et al. | 536/1.11 |
| 5,527,524 | 6/1996 | Tomalia et al. | 424/1.33 |
| 5,620,858 | 4/1997 | Armstrong et al. | 435/7.8 |
| 5,679,653 | 10/1997 | Armstrong et al. | 514/53 |
| 5,714,166 | 2/1998 | Tomalia et al. | 424/486 |
| 5,807,971 | 9/1998 | Gozzini et al. | 528/332 |
| 5,834,020 | 11/1998 | Margerum et al. | 424/484 |

FOREIGN PATENT DOCUMENTS

| | | |
|---|---|---|
| 93/08209 | 4/1993 | WIPO . |

OTHER PUBLICATIONS

Abbas, S.A., et al., "Tumor–Associated Oligosaccharides I: Synthesis of Sialyl–Lewis[a] Antigenic Determinant," Sialic Acids Proc. Japan–German Symp. Berlin, pp. 22–23 (1988).

Altman, D.G., "Comparing groups–continuous data," Practical Statistics for Medical Research, 1st ed., New York, Chapman and Hall: pp. 179–228 (1991).

Amvam–Zollo, et al., "*Streptococcus pneumoniae* Type XIV Polysaccharide: Synthesis of a Repeating Branched Tetrasaccharide with Dioxa–Type Spacer Arms," Carbohy. Res., vol. 150 pp. 199–212 (1986).

Armstrong, et al., "Maintenance of Biological Activity of Pertussis Toxin Radioiodinated While Bound to Fetuin–Agarose," Infect. Immun., vol. 55, pp. 1294–1299 (1987).

Armstrong, et al., "Investigation of Shiga–like Toxin Binding to Chemically Synthesized Oligosaccharide Sequences," J. Infect Dis., vol. 164, pp. 1160–1167 (1991).

Boyd, et al., "Vertoxdin Receptor Glycolipid in Human Renal Tissue," Nephron, vol. 51, pp. 207–210 (1989).

Calderwood, et al., Nucleotide sequence of the Shiga–like toxin genes of *Escherichia coli*, Proc. Natl. Acad. Sci. (USA), vol. 84, pp. 4364–4368 (1987).

Chernyak, Y.A., et a., "A New Type of Carbohydrate–Containing Synthetic Antigen: Synthesis of Carbohydrate–Containing Polyacrylamide Copolymers having the Specificity of 0:3 and 0:4 Factors of Salmonella," Carbo. Res., vol. 128, pp. 269–282 (1984).

Cimolai, et al., The Journal of Pediatrics, vol. 117 pp. 676 (1990).

Cohen, et al., "Roles of Globotriosyl– and Galabiosylceramide in Verotoxin Binding and High Affinity Interferon Receptor," J. Biol. Chem., vol. 262, pp. 17088–17091 (1987).

Cox, et al., "A New Synthesis of 4–0–α–D–Galactopyranosyl–D–Galacto–Pyranose," Carbohy. Res., vol. 62, pp. 245–252 (1978).

Dahmén, J., et al., "Synthesis of Spacer–Arm, Lipid, and Ethyl Glycosides of the Trisacchride Portion [α–D–Gal(1→4)–β–D–Gal–(1→4)–β–D–Glc] of the Blood–Group $P^k$ Antigen: Preparation of Neoglycoproteins," Carboh. Res., vol. 127, pp. 15–25 (1984).

Dahmén, J., et al., "2–Bromoethyl glycosides: applications in the synthesis of spacer–arm glycosides," Carboh. Res., vol. 118, pp. 292–301 (1983).

DeGrandis, et al., "Globotetraosylceramide is Recognized by the Pig Edema Disease Toxin," J. Biol. Chem., vol. 264, pp. 12520–12525 (1989).

Ekborg, G., et al., "Synthesis of Three Disacharides for the Preparation of Immunogens bearing Immunodeterminants Known to Occur on Glycoproteins," Carboh. Res., vol. 110, pp. 55–67 (1982).

Fernandez–Santana, V., et al., "Glycosides of Monoallyl Diethylene Glycol. A New Type of Spacer Group for Synthetic Oligosaccharides," J. Carboh. Chem., vol. 8, No. 3, pp. 531–537 (1989).

Fügedi, P., et al., "Thioglycosides as Glycosylating Agents in Oligosaccharide Synthesis," Glycoconjugate J., vol. 4, pp. 97–108 (1987).

Gannon, et al., "Molecular cloning and nucleotide sequence of another variant of the *Escherichia coli* Shiga–like toxin II family," J. Gen. Microbiol., vol. 136, pp. 1125–1135 (1990).

(List continued on next page.)

*Primary Examiner*—Howard C. Lee
*Attorney, Agent, or Firm*—Burns, Doane, Swecker & Mathis, L.L.P.

[57] ABSTRACT

Compounds which bind to shiga-like toxins (SLT) associated with enteric *E. coli* infection, compositions including the compounds, methods for the neutralization of (SLT) in a patient, and methods for the diagnosis of enteric *E. coli* infection are disclosed. The compounds include a core molecule bound to a plurality of linker arms, which in turn are bound to a plurality of bridging moieties, which in turn are bound to two or three di- or tri-saccharide moieties. The di- or tri-saccharide moieties themselves are active in binding to the SLTs. The presence of a plurality of bridged dimers of the di- and tri-saccharides is responsible for the increased binding affinity of the compounds relative to the di- and tri-saccharides themselves. The compounds, when administered in a timely fashion to a patient suffering from enteric *E. coli* infection, inhibit progression of this infection into hemolytic uremic syndrome (HUS).

19 Claims, 11 Drawing Sheets

OTHER PUBLICATIONS

Garegg, P.J., et al., "A Synthesis of 8–Methoxycarbonyloct–1–yl O–α–D–Galactopyranosyl–(1→3)–O–β–D–Galactopyranosyl–(1→4)–2–Acetamido–2–Deoxy–β–D–Glucopyranoside," Carboh. Res., vol. 136, pp. 207–213 (1985).

Garegg, P.J., et al., "Synthesis of 6– and 6'–deoxy derivatives of methyl 4–O–α–D–galactopyranosyl–β–D–Galactopyranoside for studies of inhibition of pyelonephritogenic fimbriated *E. coli* adhesion to urinary epithelium–cell surfaces," Carboh. Res., vol. 137, pp. 270–275 (1985).

Hansen, et al., "Di–, Tri–, and Tetravalent Dendritic Galabiosides That Inhibit Hemagglutination by *Streptococcus suis* at Nanomolar Concentration," J. Am. Chem. Soc., vol. 119, pp. 6974–6979 (1997).

Head, S., et al., "Modification of the Glycolipid–Binding Specificity of Vero Cytotoxin by Polymyxin B and Other Cyclic Amphipathic Peptides," Infect. Immunol., vol. 58, pp. 1532–1537 (1990).

Head, S., et al., "Purification and characterization of verocytotoxin 2," FEMS Microbiol. Lett., vol. 51, pp. 211–216 (1988).

Ito, et al., "Cloning and nucleotide sequencing of Vero toxin 2 variant genes from *Escherichia coli* O91:H21 isolated from patient . . ." Microb. Pathog., vol. 8 pp. 47–60 (1990).

Jacewicz, et al., "Pathogenesis of Shigella Diarrhea," J. Exp. Med., vol. 163, pp. 1391–1404 (1986).

Jackson, et al., "Nucleotide sequence analysis of the structural genes for Shiga–like toxin I encoded by bacteriophage 933J . . . ," Microb. Pathog., vol. 2 pp. 147–153 (1987).

Jacquinet, et al., "Synthesis of Blood–group Substances, Part 11. Synthesis of the Trisaccharide O–α–D–Galactopyranosyl–(1→3)–O–β–D–Galactopyranosyl–(1→4)–2–. . . ," J.C.S. Perkin, vol. I, pp. 326–330 (1981).

Kameyama, et al., "Total synthesis of sialyl Lewis X," Carboh. Res., vol. 209 pp. c1–c4 (1991).

Karmali, et al., "Sensitive Method for Detecting Low Numbers of Verotoxin–Producing *Escherichia coli* in Mixed Cultures . . . ," J. Clin. Microbiol., vol. 22, pp. 614–619 (1985).

Koike, et al., "Total Synthesis of Globotriaosyl–E and Z–Ceramides and Isoglobotriaosyl–E–Ceramide," Carbohydr. Res., vol. 163, pp. 189–208 (1987).

Lee, et al., "Synthesis of 3–(2–Aminoethylthio)Propyl Glycosides," Carboh. Res., vol. 37, pp. 193–201 (1974).

Lemieux, et al., "The properties of a Synthetic Antigen Related to the Human Blood–Group Lewis A," J. Am. Chem. Soc., vol. 97, pp. 4076–4083 (1975).

Ling, et al., "Structure of the Shiga–like Toxin I B–Pentamer Complexed with an Analogue of Its Receptor $Gb_3$," vol. 37, pp. 1777–1788 (1998).

Lindberg, et al., "Identification of the Carbohydrate Receptor for Shiga Toxin Produced by *Shigella dysenteriae* Type 1," J. Biol. Chem., vol. 262, pp. 1779–1785 (1987).

Lingwood, et al., "Glycolipid Binding of Purified and Recombinant *Escherichia coli* Produced Verotoxin in Vitro," J. Biol. Chem., vol. 262, pp. 8834–8839 (1987).

Nilsson, et al., "Immobilization of Reducing Sugars as Toxin Binding Agents," Bioconj. Chem., vol. 8, No. 4, pp. 466–471 (1997).

Nyholm, et al., "Two distinct binding sites for globotriaosyl ceramide on verotoxins: identification by molecular modelling . . . ," Chem. and Biol., vol. 3, pp. 263–275 (1996).

Okamoto, et al., "Glycosidation of Sialic Acid," Tetrahedron, vol. 47 pp. 5835–5857 (1990).

Oku, et al., "Purification and some properties of a Vero toxin from a human strain of *Escherichia coli* that is immunologically . . . ," Microb. Pathog., vol. 6, pp. 113–122 (1989).

Paulsen, H., "Advances in Selective Chemical Syntheses of Complex Oligosaccharides," Angew. Chem. Int. Ed. Eng., vol. 21, pp. 155–173 (1982).

Paulsen, H., et al., "Synthese Von Oligosacchariden–Determinanten Mit Amid–spacer Vom Typ Des T–Antigens," Carbohydr. Res., vol. 104, pp. 195–219 (1982).

Rana, S. S., et al., "Synthesis of Phenyl 2–Acetamido–2–Deoxy–3–O–α–L–Fucopyranosyl–β–D–Glucopyranoside and Related Compounds," Carboh. Res., vol. 91, pp. 149–157 (1981).

Roboson, et al., "Influence of antidiarrheal and antimicrobial medications on the hemorrhagic colitis associated with hemolytic–uremic syndrome," J. Petitur., vol. 117, pp. 675–676 (1990).

Samuel, et al., "Comparison of the Glycolipid Receptor Specificities of Shiga–Like Toxin Type II and Shiga–Like Toxin Type II Variants," Infect. Immunol., vol. 58, pp. 611–618 (1990).

Schaubach, R. et al., "Tumor–Associated Antigen Synthesis: Synthesis of the Gal–α–(1→3)–Gal–β–(1→4)–GlcNAc Epitope A Specific Determinant for Metastatic Progression?," Lievigs. Am. Chem., pp. 607–614 (1991).

Schmitt, C.K., et al., "Two Copies of Shiga–Like Toxin II–Related Genes Common in Enterohemorrhagic *Escherichia coli* Strains Are Responsible for the Antigenic Heterogeneity of the O157:H Strain E32511," Infect. Immun., vol. 59, pp. 1065–1073 (1991).

Schmidt, R.R., "New Methods for the Synthesis of Glycosides and Oligosaccharides–Are There Alternatives to the Koenigs–Knorr Method?," Angew. Chem. Int. Ed. Eng., vol. 25, pp. 212–235 (1986).

Scotland, S.M., et al., "Two Distinct Toxins Active on Vero Cells from *Escherichia Coli* 0157," Lancet, vol. ii, pp. 885–886 (1991).

Strockbine, N.A., et al., "Cloning and Sequencing of the Genes for Shiga Toxin from *Shigella dysenteriae* Type I," J. Bacterial., vol. 170, pp. 1116–1122 (1988).

Waddell, T., et al., "Globotriosyl Ceramide is Specifically Recognized by the *Escherichia Coli* Verocytotoxin 2," Biochem. Biophys. Res. Comm., vol. 152, pp. 674–679 (1988).

Waddell, T. et al., "Induction of verotoxin sensitivity in receptor–deficient cell lines using the receptor glycolipid globotriosylceramide," Proc. Natl. Acad. Sci. (USA), vol. 87, pp. 7898–7901 (1990).

Weinstein, D.L., et al., "Cloning and Sequencing of a Shiga–Like Toxin Type II Variant from an *Escherichia coli* Strain Responsible for Edema Disease of Swine," vol. 170, pp. 4223–4230 (1988).

Inhibitor "Starfish" Activity
Comparison of Verotoxin-1 Affinity with Various Ligands General Point:- the binding subunits of VT-1 and Shiga toxin are identical VT-1 + $P^kOMe$ $\rightleftharpoons$ [complex], $K_d = 10^{-3}$ St. Hilaire, P. M., Boyd, M. K., and Toone, E. J., *Biochemistry*, 1994, 33, 14452-14463.

VT-1 + $P^kOMe$-$P^kOMe$ $\rightleftharpoons$ [complex], $K_d = 3 \cdot 10^{-5}$ P. Kitov and D.R. Bundle unpublished data.

Shiga toxin + Cell $\rightleftharpoons$ [complex], $K_d = 10^{-9}$

Fuchs, G., Mobassaleh, M., Donohue-Rolfe, A., Montgomery, R. K., Gerard, R. J., and Keusch, G. T. *Infect. Immun.* 1986, 53, 372-377.

VT-1 + [starfish ligand] $\rightleftharpoons$ [complex], $K_d = 10^{-10}$

P. Kitov and D.R. Bundle unpublished data

FIGURE 2

TREATMENT OF BACTERIAL DYSENTERY

BACKGROUND OF THE INVENTION

Field of the Invention

This invention relates to the treatment of diarrhea caused by pathogenic *E. coli* infection. More specifically, this invention relates to methods for the neutralization of shiga-like toxins (SLT) associated with enteric *E. coli* infection which methods inhibit progression of this infection into hemolytic uremic syndrome (HUS).

References

The following references are cited in the application as numbers in brackets ([ ]) at the relevant portion of the application.

1. Karmali, M. A. et al., *J. Clin. Microbiol.* 22:614–619 (1985).
2. Head, S., et al., *Infect Immunol.* 58:1532–1537 (1990).
3. Samuel et al., *Infect Immunol.* 58:611–618 (1990).
4. Altman, D. G. *Practical Statistics for Medical Research* 1st ed. New York, Chapman and Hall: 179–228 (1991).
5. Calderwood, et al., *Proc. Natl. Acad. Sci. (USA)*, 84:4364–4368 (1987)
6. Jackson, et al., *Microb. Pathog.*, 2:147–153 (1987)
7. Strockbine, et al., *J. Bacterial.*, 170:1116–1122 (1988)
8. Robson, et al., *J. Petitur.*, 117:675–676 (1990)
9. Cembalo, et al., *J. Petitur.*, 117:676 (1990)
10. Armstrong, et al., International Patent Application Publication No. WO 93/08209, for "DIAGNOSIS AND TREATMENT OF BACTERIAL DYSENTERY, published Apr. 29, 1993
11. Lamas, R. U., et al., "The properties of a 'synthetic' antigen related to the blood-group Lewis A", *J. Am. Chem. Soc.*, 97:4076–83 (1975).
12. Lamas, R. U., et al., "Glycoside-Ether-Ester Compounds", U.S. Pat. No. 4,137,401, issued Jan. 30, 1979.
13. Lamas, R. U., et al., "Artificial Oligosaccharide Antigenic Determinants", U.S. Pat. No. 4,238,473, issued Dec. 9, 1980.
14. Lamas, R. U., et al., "Synthesis of 2-Amino-2-Deoxyglycoses and 2-Amino-2-Deoxyglycosides from glycals", U.S. Pat. No. 4,362,720, issued Dec. 7, 1982.
15. Cox, D., et al. "A New Synthesis of 4-O-α-D-Galactopyranosyl-D-Galacto-Pyranose", *Carbohy. Res.*, 62: 245–252 (1978).
16. Dahmén, J., et al., "Synthesis of space arm, lipid, and ethyl glycosides of the trisaccharide portion [α-D-Gal-(1–4)-β-D-Gal(1–4)-β-D-Glc] of the blood group $p^k$ antigen: preparation of neoglycoproteins", *Carbohydrate Research*, 127: 15–25 (1984).
17. Garegg, P. J., et al., "A Synthesis of 8-Methoxycarbonyloct-1-yl O-α-D-Galactopyranosyl-(1–3)-O-β-D-Galactopyranosyl-(1–4)-2-Acetamido-2-Deoxy-β-D-Glucopyranoside", *Carbohy. Res.*, 136: 207–213 (1985).
18. Garegg, P. J., et al., "Synthesis of 6- and 6'-deoxy derivatives of methyl 4-O-α-D-galactopyranosyl-β-D-galactopyranoside for studies of inhibition of pyelonephritogenic fimbriated *E. coli* adhesion to urinary epithelium-cell surfaces", *Carbohy. Res.*, 137: 270–275 (1985).
19. Jacquinet, J. C., et al., "Synthesis of Blood-group Substances, Part 11. Synthesis of the Trisaccharide O-α-D-Galactopyranosyl-(1–3)-O-β-D-galactopyranosyl-(1–4)-2-acetamido-2-deoxy-D-glucopyranose", *J.C.S. Perkin*, I: 326–330 (1981).
20. Koike, K., et al., "Total Synthesis of Globotriaosyl-E and Z-Ceramides and Isoglobotriaosyl-E-Ceramide," *Carbohydr. Res.*, 163: 189–208 (1987).
21. Schaubach, R., et al., "Tumor-Associated Antigen Synthesis: Synthesis of the Gal-α-(1–3)-Gal-β-(1–4)-GlcNAc Epitope. A specific Determinant for Metastatic Progression?", *Liebigs Ann. Chem.*, 607–614 (1991).
22. Ratcliffe, R. M., et al., "Sialic Acid Glycosides, Antigens, Immunoadsorbents, and Methods for Their Preparation", U.S. Pat. No. 5,079,353, issued Jan. 7, 1992.
23. Okamoto, K., et al., "Glycosidation of Sialic Acid," *Tetrahedron*, 47: 5835–5857 (1990).
24. Abbas, S. A., et al., "Tumor-Associated Oligosaccharides I: Synthesis of Sialyl-Lewis$^a$ Antigenic Determinant", *Sialic Acids, Proc. Japan-German Symp.* Berlin 22–23 (1988).
25. Paulsen, "Advances in Selective Chemical Syntheses of Complex Oligosaccharides", *Angew. Chem. Int. Ed. Eng.*, 21:155–173 (1982).
26. Schmidt, "New Methods for the Synthesis of Glycosides and Oligosaccharides—Are There Alternatives to the Koenigs-Knorr Method?", *Angew. Chem. Int. Ed. Eng.*, 25:212–235 (1986).
27. Fügedi, P., et al., "Thioglycosides as Glycosylating Agents in Oligosaccharide Synthesis", *Glycoconjugate J.*, 4:97–108 (1987).
28. Kameyama, A., et al., "Total synthesis of sialyl Lewis X", *Carbohydrate Res.*, 209: c1–c4 (1991).
29. Ekborg, G., et al., "Synthesis of Three Disaccharides for the Preparation of Immunogens bearing Immunodeterminants Known to Occur on Glycoproteins", *Carbohydrate Research*, 110: 55–67 (1982).
30. Dahmén, J., et al., "2-Bromoethyl glycosides: applications in the synthesis of spacer-arm glycosides", *Carbohydrate Research*, 118: 292–301 (1983).
31. Rana, S. S., et al., "Synthesis of Phenyl 2-Acetamido-2-Deoxy-3-O-α-L-Fucopyranosyl-β-D-Glucopyranoside and Related Compounds", *Carbohydrate Research*, 91:149–157 (1981).
32. Amvam-Zollo, P., et al., "Streptococcus pneumoniae Type XIV Polysaccharide: Synthesis of a Repeating Branched Tetrasaccharide with Dioxa-Type Spacer-Arms", *Carbohydrate Research*, 150:199–212 (1986).
33. Paulsen, H., "Synthese von oligosaccharid-determinanten mit amid-spacer vom typ des T-antigens", *Carbohydr. Res.*, 104:195–219 (1982).
34. Chemyak, A. Y., et al., "A New Type of Carbohydrate-Containing Synthetic Antigen: Synthesis of Carbohydrate-Containing Polyacrylamide Copolyrners having the Specificity of 0:3 and 0:4 Factors of Salmonella", *Carbohydrate Research*, 128:269–282 (1984).
35. Fernandez-Santana, V., et al., "Glycosides of Monoallyl Diethylene Glycol. A New type of Spacer group for Synthetic Oligosaccharides", *J. Carbohydrate Chemistry*, 8(3):531–537 (1989).
36. Lee, R. T., et al., "Synthesis of 3-(2-Aminoethylthio) PropylGlycosides", *Carbohydrate Research*, 37:193–201 (1974).
37. Gannon, et al., *J. Gen. Microbiol.*, 136:1125–1135 (1990)
38. Weinstein, et al., *J. Bacterial.*, 170:4223–4230 (1988)
39. Ito, et al., *Microb. Pathog.*, 8:47–60 (1990)
40. Head, et al., *FEMS Microbiol. Lett.*, 51:211–216 (1988)

41. Schmitt, et al., *Infect. Immun.*, 59:1065–1073 (1991)
42. Scotland, et al., *Lancet*, ii:885–886 (1991)
43. Oku, et al., *Microb. Pathog.*, 6:113–122 (1989)
44. Boyd, et al., *Nephron*, 51:207–210 (1989)
45. DeGrandis, et al., *J. Biol. Chem.*, 264:12520–12525 (1989)
46. Waddell, et al., *Biochem. Biophys. Res. Comm.*, 152:674–679 (1988)
47. Lingwood, et al., *J. Biol. Chem.*, 262:8834–8839 (1987)
48. Waddell, et al., *Proc. Natl. Acad. Sci. (USA)*, 87:7898–7901 (1990)
49. Cohen, et al., *J. Biol. Chem.*, 262:17088–17091 (1987)
50. Jacewicz, et al., *J. Exp. Med.*, 163:1391–1404 (1986)
51. Lindberg, et al., *J. Biol. Chem.*, 262:1779–1785 (1987)
52. Armstrong, G. D. et al., *Infect. Immun.*, 55:1294–1299 (1987)
53. Armstrong, G. D. et al., *J. Infect. Dis.* 164:1160–1167 (1991)

The disclosure of the above publications, patents and patent application are herein incorporated by reference in their entirety to the same extent as if the language of each individual publication, patent and patent application were specifically and individually included herein.

State of the Art

Diarrhea caused by strains of pathogenic *E. coli* has been found to be associated with the production of a variety of enterotoxins. Some pathogenic *E. coli* produce enterotoxins that are closely related to the shiga toxin associated with Shigella-caused dysentery. The first member of the family of shiga-like toxins (SLT) to be isolated was cytotoxic for African Green Monkey (Vero) cells and was originally called verotoxin. Since its structural similarity to shiga toxin has been established by sequencing of the relevant genes, this toxin is now more commonly called shiga-like toxin I (SLTI) [5,6,7].

Additional members of the SLT family have subsequently been isolated that can be distinguished serologically, on the basis of gene sequence, or on host specificity [37–43]. Various types of SLTII have been described and have been assigned various designations depending on the strain of *E. coli* from which they are isolated and the host affected. Thus variants have been designated SLTII; vtx2ha; SLTIIvh; vtx2hb; SLTIIc; SLTIIvp and so forth.

All of the SLT's are multimeric proteins composed of an enzymatic (A) subunit and multiple (B) subunits. The B oligomer is the binding portion of the toxin that allows it to bind to host cell receptors. The B subunits of SLTI, SLTII and SLTIIvh recognize host cell globoseries glycolipid receptors containing at minimum the disaccharide subunit αGal(1–4)βGal at the non-reducing terminus; SLTIIvp has been shown to bind to the receptors containing this subunit but not necessarily to the non-reducing end [2, 44–51]. The A subunit has an enzymatic activity (N-glycosidase) that depurinates 28S ribosomal RNA in mammalian cells. This enzymatic activity abolishes the ability of the toxin-infected cell to perform protein synthesis.

The site for SLT action is endothelial cells found in the kidneys and mesenteric vasculature, and SLTs may cause damage that can result in renal failure and hemoglobin in the urine. SLTs are the causative agent in the hemolytic-uremic syndrome. SLTs may also be partially involved in the pathogenesis of hemorrhagic colitis (bloody diarrhea). The hemolytic uremic syndrome (HUS) is the leading cause of acute renal failure in childhood and affects approximately 7–10% of children in the 5–10 days following infection with *E. coli* 0157:H7 and other verotoxin/shiga-like toxin producing *E. coli* (VTEC).

Recent attention regarding such pathogenic *E. coli* has focussed on the known correlation between *E. coli* contamination of certain meats and subsequent infection in humans after ingestion of this meat. The problem is particularly acute with regard to hamburger meat where ingestion of undercooked meat has been found to be the causative factor in the infection. This problem is compounded by the fact that the rapid progression of the pathogenic *E. coli* infection into HUS via the expression of the SLTs suggests the hypothesis that initial colonization of the intestinal tract is followed by endothelial injury and subsequent kidney involvement via the transmembrane delivery of the SLT toxin into the blood stream of the infected individual.

As a complicating factor, the art suggests against the use of antibiotics in the treatment of enterohemorrhagic *E. coli* infection [8]. The use of antimotility drugs also appears to be counterproductive [9].

An approach to treating the effects of the infection is to bind the toxin, thereby protecting cells from being damaged. Studies have shown that the functional receptor for SLTs is the glycolipid Gb3. The carbohydrate binding component of the toxin is a donut shaped pentameric structure built from five identical subunits. The *E. coli* verotoxin (VTI) has been crystallized with the Pk trisaccharide and three distinct binding sites per subunit revealed occupancy by trisaccharide [H. Ling, et al., *Biochemistry*, 37:1777–1788 (1998)]. Docking studies [P-G. Nyholm, et al., *Chemistry and Biology*, 3:263–275 (1996)] also suggest an additional Pk recognizing domain on the protein surface. VT1 is a good model system to study multivalent interactions in the search for tight binding inhibitors of bacterial toxins.

Various reducing sugars, including monosaccharides, disaccharides and trisaccharides, have been bound to SLTs. Several prior attempts to design multivalent inhibitors of receptor-saccharide binding have used monovalent oligosaccharides that are glycosidically linked to a functionalized tether to provide multianntenary ligand presentation. The verotoxin system cited above (VTI) illustrates that the assumption of a uniform binding motif may not always occur. Further, the optimum site for tethering ligands need not be the anomeric center of the terminal reducing sugar.

Toxins have been bound to a solid support containing an immobilized reducing sugar (Nilsson et al., *Bioconjugate Chem.*, 8:466–471 (1997)). Pharmaceutically inert affinity supports that include an αGal(1→4)βGal subunit have been administered to infected patients to treat the infection [10]. The support passes into the intestinal tract of the patient whereupon the αGal(1→4)βGal subunit binds the Shiga-like toxin. Subsequently, the toxin bound to this solid support is eliminated from the body as part of the stool. This procedure removes the toxins from the body which, in turn, inhibits manifestation of the conditions associated with toxin accumulation.

U.S. Pat. No. 5,679,653 to Armstrong et al. discloses the use of various compositions which include αGal(1–4)βGal subunits, and the use of these compositions to diagnose and treat enteric infections caused by *E. coli* that produce Shiga-like toxins. These compositions also include a solid support to which the subunits are bound, optionally through the use of a linker arm.

Dendrimers including multiple carbohydrate moieties with high affinity for lectins on the surface of some bacteria have been prepared. Hansen et al., *J. Am. Chem. Soc.*, 119:6974–6979 (1997). The multivalent dendrimers were reported to be hundreds of times more efficient than the monomeric compounds in binding the surface-bound lectins. However, the use of multivalent dendrimers has not been applied to the binding of toxins associated with enterohemorrhagic E. coli infections.

Notwithstanding the significant advances made by these reported methods, further advances in the treatment of enterohemorrhagic E. coli infections are needed in order to reduce the occurrence of HUS and the high morbidity levels associated therewith.

SUMMARY OF THE INVENTION

This invention is directed to compounds and pharmaceutical compositions useful for binding to a Shiga-like toxin ("SLT"), and methods of preparation and use thereof to diagnose and/or treat HUS arising from enterohemorrhagic E. coli infection.

The compounds include a multifunctional core molecule with between 3 and 20 active sites for coupling to a linker arm, between 3 and 20 linker arms bound to the active sites, and bridged dimers or trimers linked to between 3 and 20 of the linker arms. The bridged dimers or trimers include at least one saccharide moiety selected from the group consisting of $\alpha Gal(1 \rightarrow 4)\beta Gal$, $\alpha Gal(1 \rightarrow 4)\beta Gal(1 \rightarrow 4)\beta GlcNAc$ and $\alpha Gal(1 \rightarrow 4)\beta Gal(1 \rightarrow 4)\beta Glc$. The dimers or trimers are bridged such that there are two or three dimers or trimers attached to each linker arm through a multifunctional molecule with two or three sites of attachment which are coupled to the saccharide and at least one site of attachment which is coupled to the linker arm. The bridging is performed with a bridging moiety which is linked to at least two dimers or trimers and one or more linker arms.

The linker arms are at least one carbon atom in length, and are preferably C6-20 straight, branched or cyclic alkanes, in which one or more of the carbons may be replaced with an O, S, or amine. The linker arms can be functionalized at one or more positions with a functional group selected from the group consisting of hydroxy, thiol, amine, carboxy, keto, thioester, ester, amide, carbamoyl, alkyl, aryl, aralkyl and alkaryl. Prior to being coupled, the bridging moiety and the linker arms must include suitable nucleophiles and leaving groups such that they can be coupled together. Such nucleophiles and leaving groups are well known to those of skill in the art. These groups are also used to couple the saccharides to the bridging molecule, using conventional carbohydrate chemistry.

The saccharides can include various functional groups. Suitable functional groups for these molecules are known to those of skill in the art, and include hydrogen bonding substituents such as deoxy, halo, amine, hydroxy, thio, guanidine and carboxy.

The compositions include a compound which binds to the toxin, a suitable carrier, and optionally, a solid support bound to the compound. The pharmaceutical compositions are preferably administered within about 3 days of presentation of the infection, more preferably, before organs other than the intestine become involved.

The methods of treatment generally involve the time critical administration of an effective amount of one or more of the compounds, or a pharmaceutical composition that includes one or more of the compounds, which may or may not be bound to a solid support or other inert carrier molecules. The infection is treated by binding the compound (s) to the toxin. The clinical incidence of HUS arising from enterohemorrhagic E. coli infection is reduced when the pharmaceutical compositions disclosed herein are administered within 3 days of presentation of the infection. Contrarily, administration of this pharmaceutical composition after this time frame or when organs other than the intestine are involved in the infection, substantially reduces the ability of this composition to reduce the incidence of HUS.

Preferably, the development of hemolytic uremic syndrome arising from enterohemorrhagic E. coli infection mediated by shiga-like toxins is inhibited in a patient using the methods disclosed herein. In a preferred embodiment the pharmaceutical composition is administered to the patient prior to organ involvement other than involvement of the intestine.

The diagnostic methods involve contacting a biological sample which is suspected of being infected with enterohemorrhagic E. coli with the compound, alone or bound to a suitable solid or other inert support. Bound toxin can be detected via known methodology. The compounds include $\alpha Gal(1 \rightarrow 4)\beta Gal$ subunits which subunits bind the SLT.

For the purposes of this invention, the presentation of the infection is determined after the identification of at least one condition associated with an SLT mediated E. coli infection. Such conditions include, for example, patients with diarrhea and one of the following: abdominal cramping, blood in the stool, rectal prolapse, detection of a verotoxin-producing E. coli in the patient's stool; ingestion of food suspected of containing a verotoxin-producing E. coli; or close contact with an individual known to have an SLT mediated infection. Preferably, the presentation of the infection is manifested by bloody diarrhea. In a particularly preferred embodiment, the initial clinical evaluation that the individual is afflicted with an SLT mediated E. coli infection is confirmed via diagnostic evaluation of the stool. One diagnostic tool commercially available for detecting SLT mediated E. coli infection is sold by Meridian Diagnostic, Inc., Cincinnati, Ohio, USA 45244 under the name Premier EHEC.

In one embodiment, the development of hemolytic uremic syndrome in a patient presenting an enterohemorrhagic E. coli infection mediated by shiga-like toxin can be inhibited by administering to the patient an effective amount of the pharmaceutical compositions disclosed herein.

BRIEF DESCRIPTION OF THE DRAWINGS

FIG. 2 is a series of illustrations demonstrating the binding affinity of Compound 22 ("Starfish") and various saccharide compositions to verotoxin, and also the binding affinity of Shiga toxins to cells.

DESCRIPTION OF THE PREFERRED EMBODIMENTS

Figure 1A:
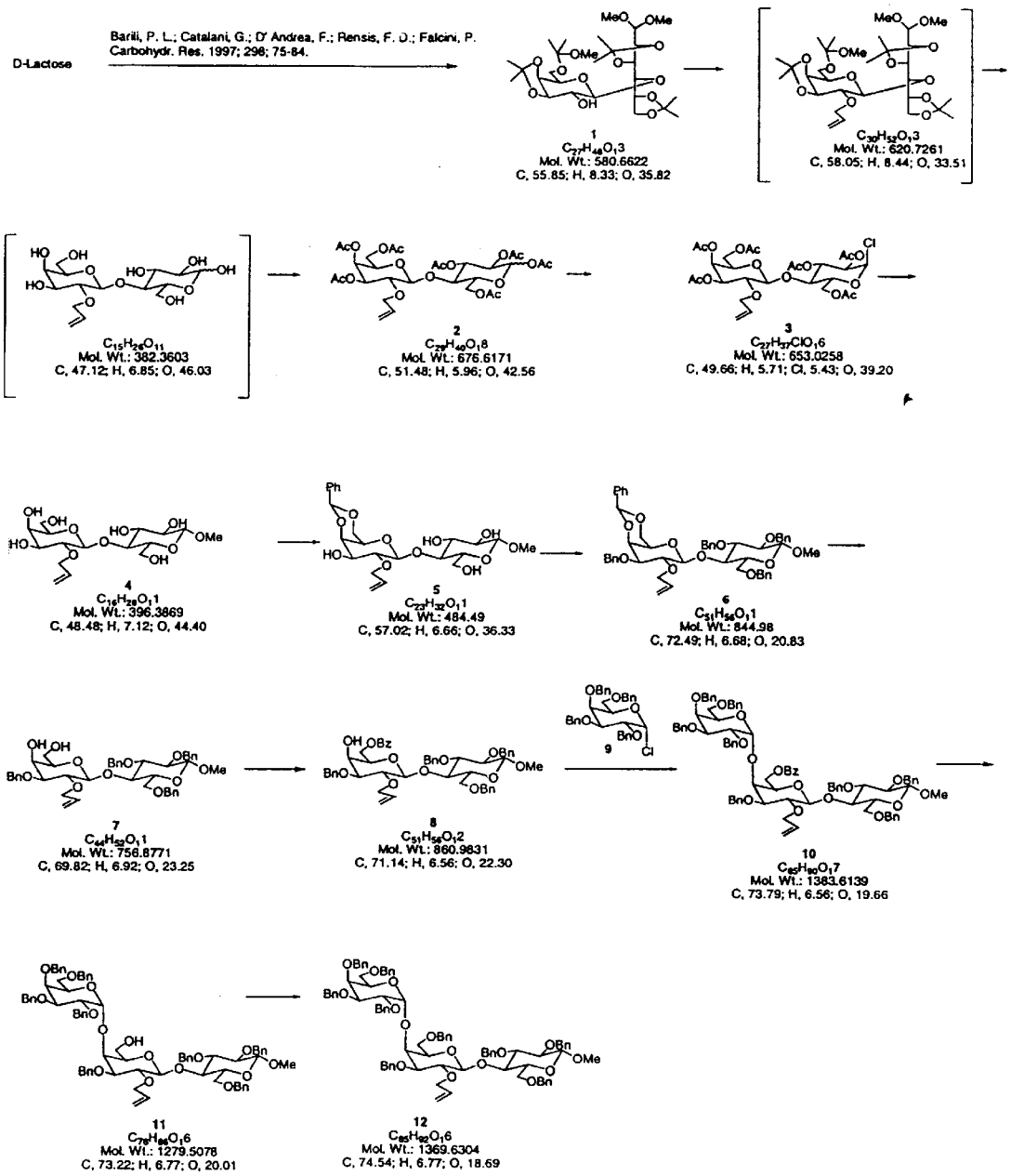
FIGS. 1a–d are schematic illustrations of a scheme for preparing a pentameric presentation of a bridged trisaccharide dimer (Compound 22).
Figure 1B:
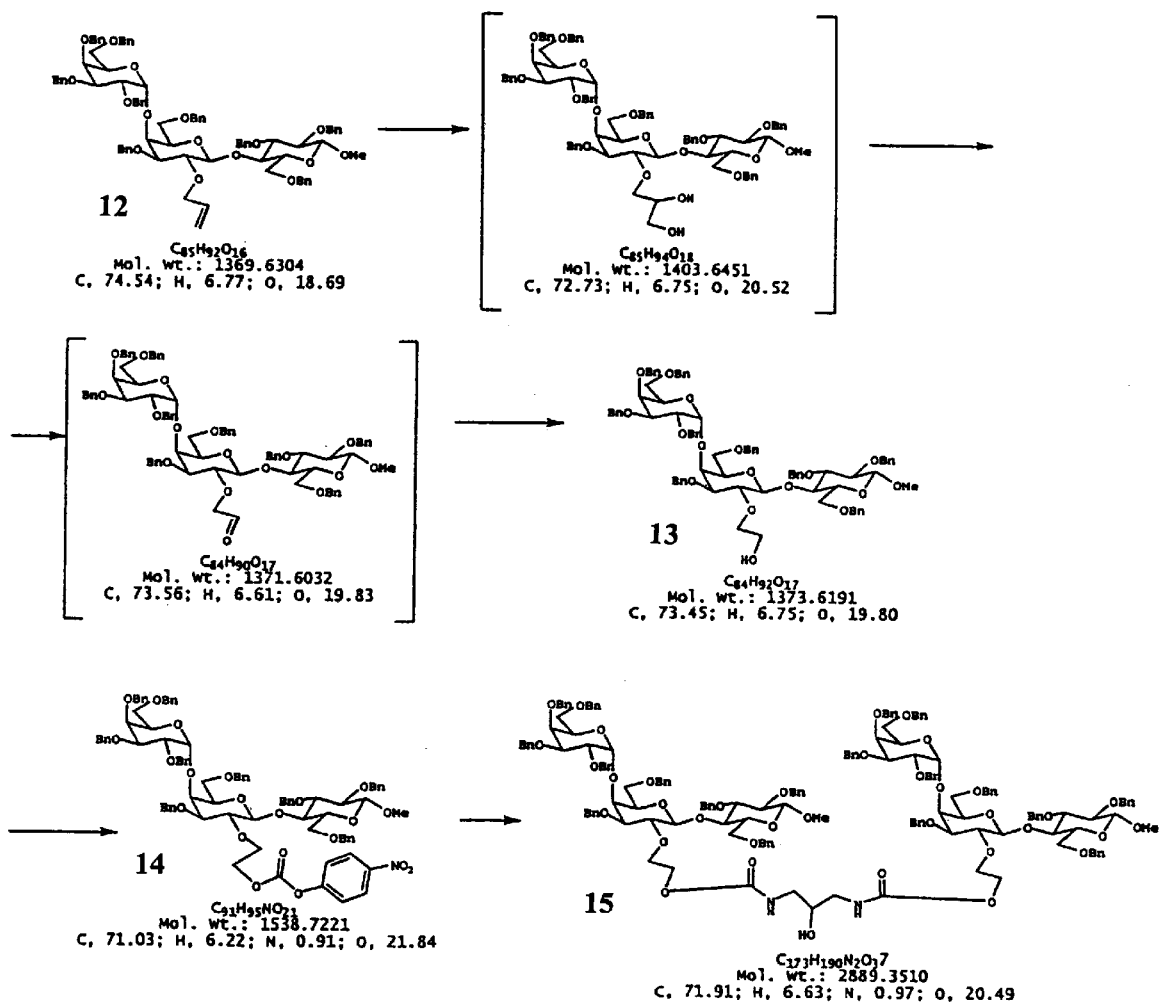
Figure 1C:
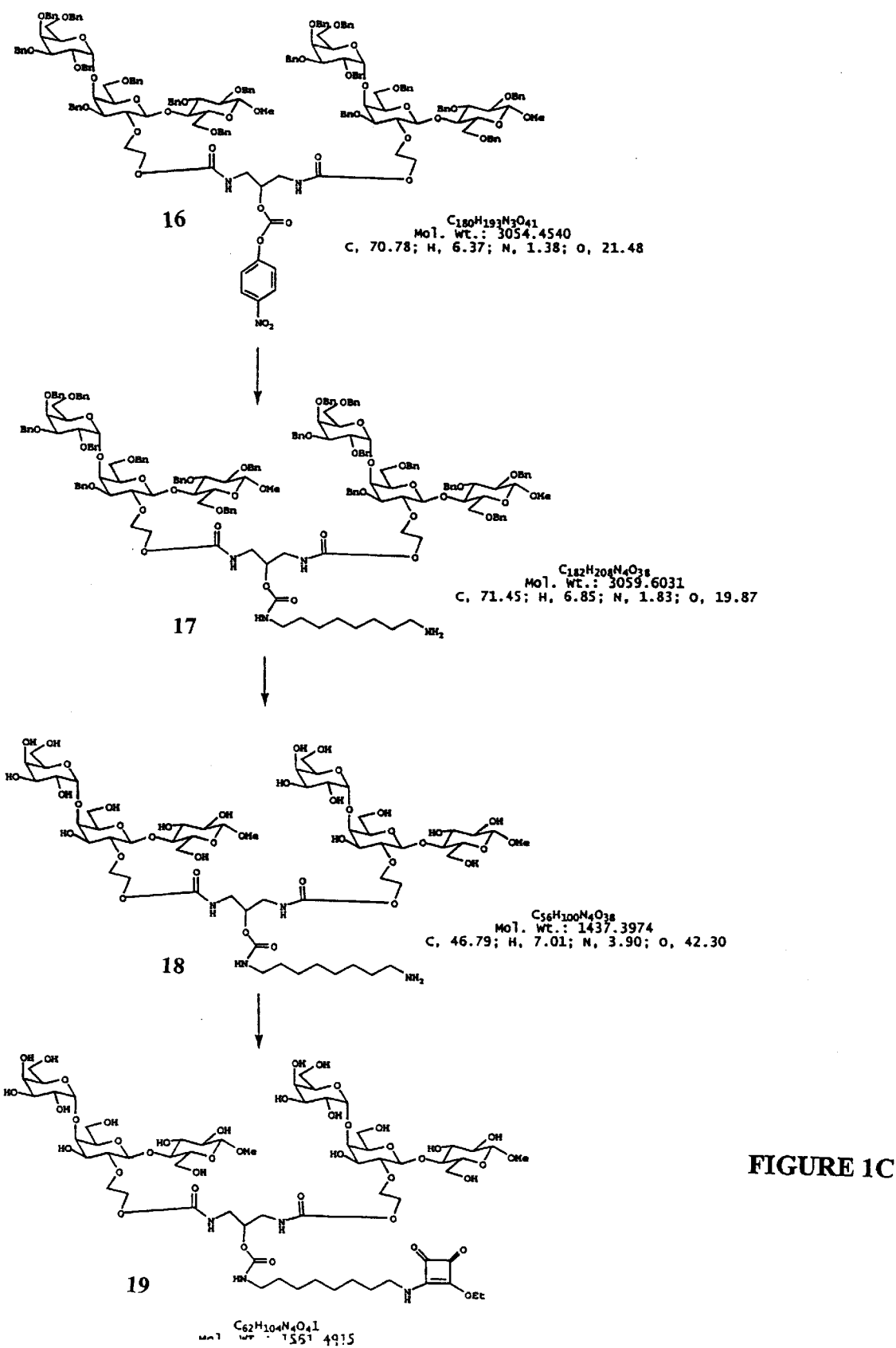
Figure 1D:
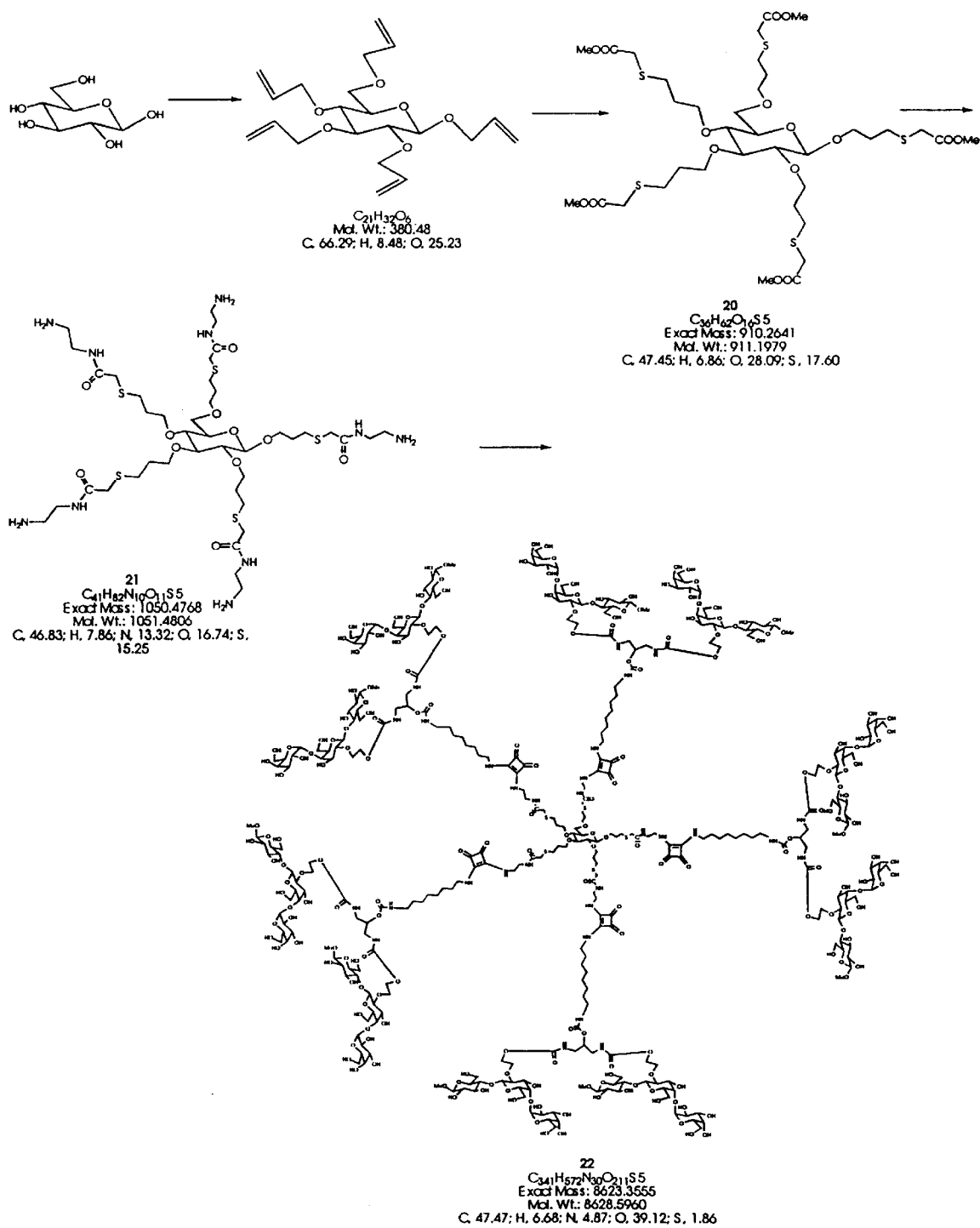
Figure 3A:
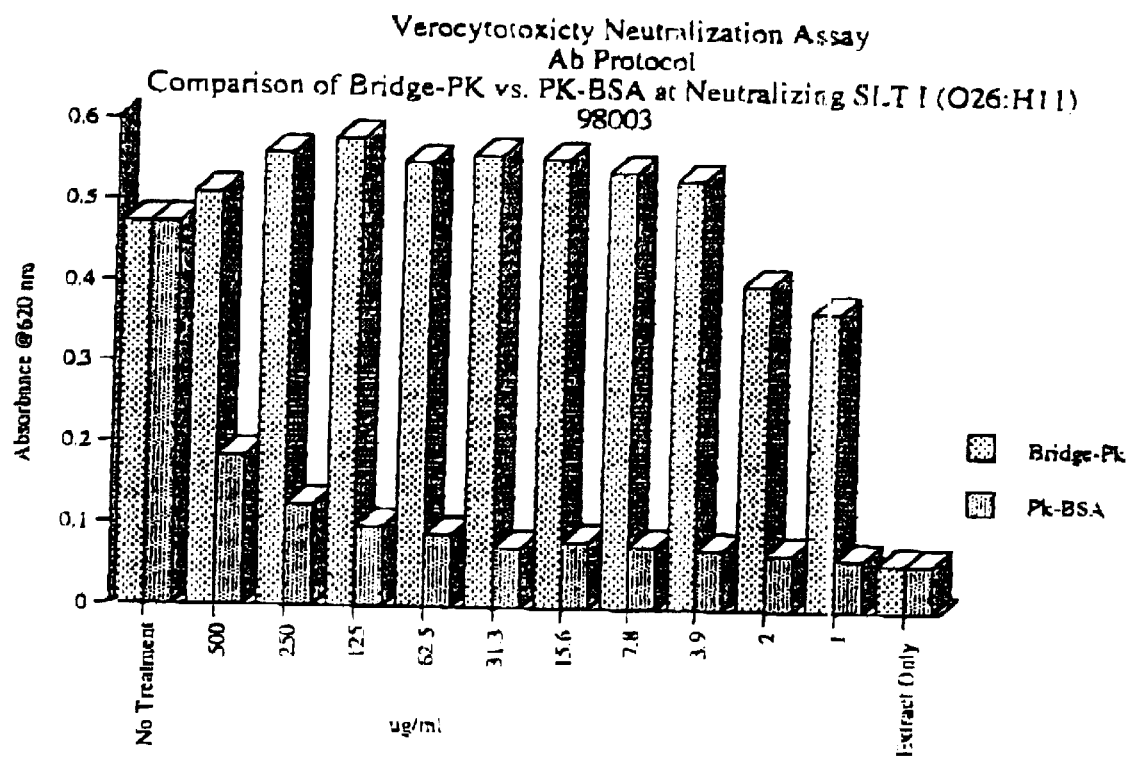
FIGS. 3a–d are graphs comparing the killing of kidney cells by SLTs with SLTs bound to a bridged Pk saccharide (lighter boxes) versus Pk saccharide linked to bovine serum albumin ("BSA") (darker boxes). The staining of viable cells was monitored at 620 nm as a function of the concentration of the compounds ($\mu$g/ml).
Figure 3B:
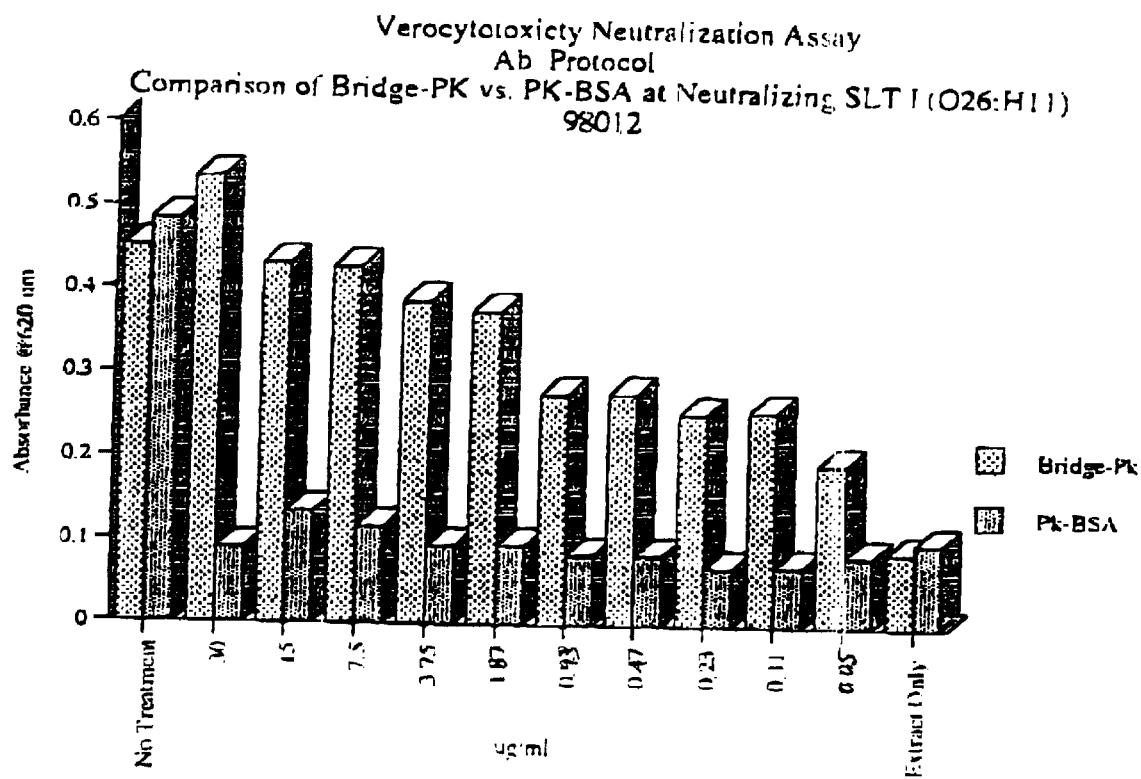
Figure 3C:
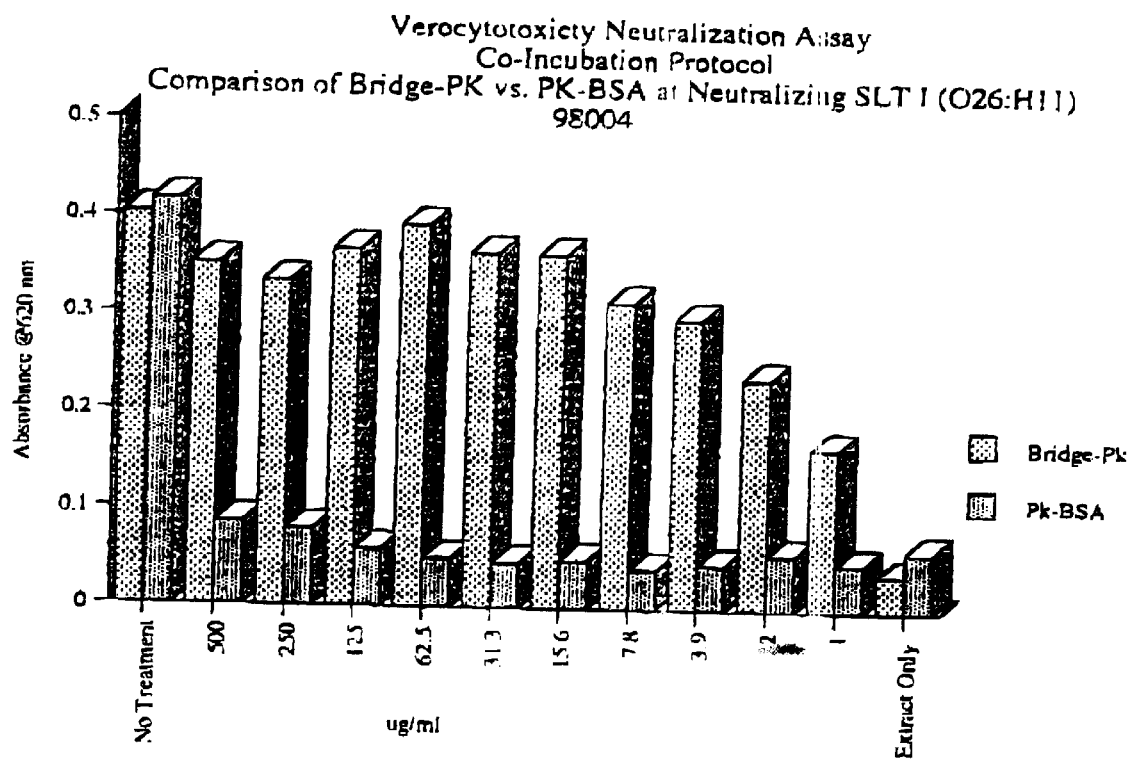
Figure 3D:
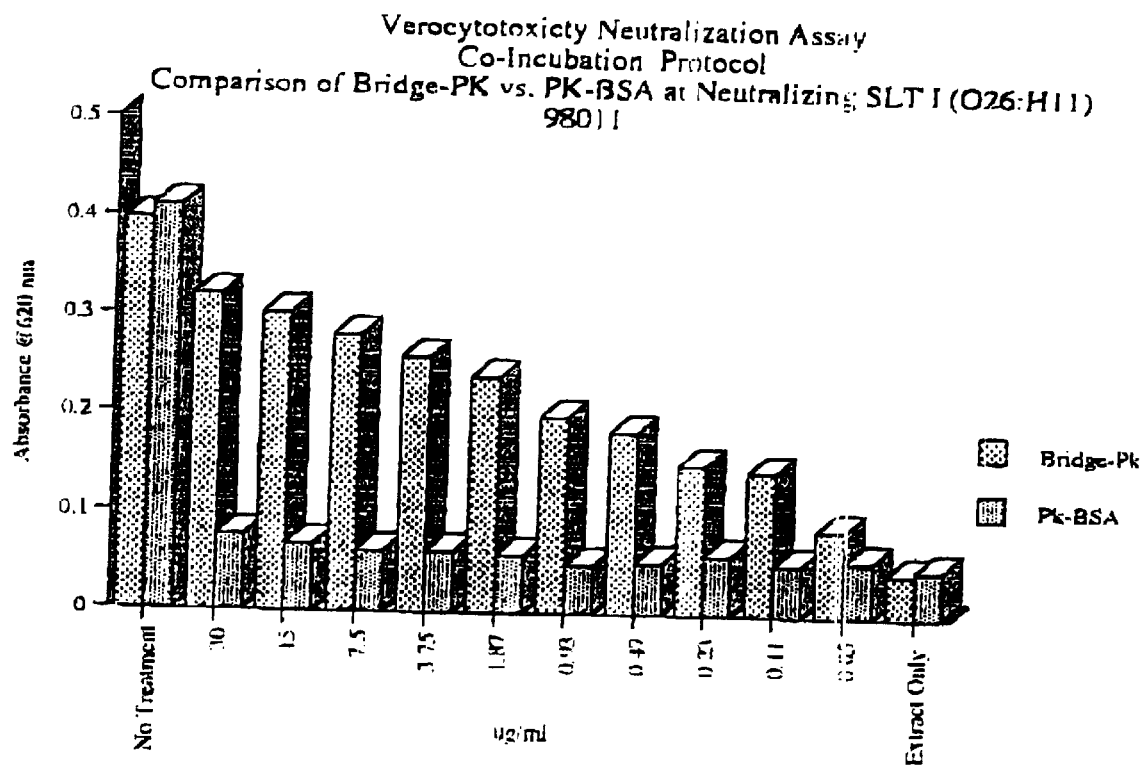

As noted above, compounds which bind to and neutralize shiga-like toxins (SLT) associated with enteric *E. coli* infection and compositions including these compounds are disclosed. Methods of preparation of these compounds, methods of inhibiting progression of this infection into hemolytic uremic syndrome (HUS), and methods of diagnosing this infection are also disclosed. However, prior to discussing this invention in further detail, the following terms will first be defined:

A. Definitions

As used herein the following terms have the following meanings:

The term "shiga-like toxin" or "SLT" or "verotoxin" refers to a group of toxins produced by enterohemorrhagic *E. coli* that resemble the Shigella-produced shiga toxins as is commonly understood in the art. These toxins comprise an enzymatically active A subunit and a multimeric receptor binding B subunit. Such SLTs include SLTI and the various grouped toxins designated in the art as SLTII.

Rapid tight binding of SLTs to compounds which include a multifunctional core molecule bound to a plurality of linker arms, which are themselves linked to bridged dimers or trimers of $P_1$ disaccharides, $P_1$ trisaccharides, or $P_k$ trisaccharides is demonstrated by the verocytotoxicity neutralization assays contained herein.

The term "organ involvement" refers to clinically defined organ involvement mediated by SLTs which correlates to the natural progression of the disease. Organs other than the intestines include, by way of example, the kidney, heart, elements of the central nervous system ("CNS") (i.e., brain, spinal cord, etc.), liver, and the like. Conventional blood chemistry tests can evaluate liver, heart, and kidney involvement whereas clinical symptoms including dementia, convulsions, disorientation, etc. are employed to determine CNS involvement.

"Hemolytic uremic syndrome" is considered to be present if there is renal injury and either hemolysis or thrombocytopenia. Renal injury requires an elevation in the serum creatinine concentration (>50 $\mu$mol/L for those less than 5 years, or >60 $\mu$mol/L for those 5–6 years) or a difference in the recorded creatinine values during the acute phase of the illness of more than 50% or at least 10 red blood cells per high power field on urine microscopy. Hemolysis is judged to be present if the hemoglobin concentration is $\leq$105 g/L or if there are red blood cell fragments on the smear or if a red blood cell transfusion was administered before the hemoglobin dropped to $\leq$105 g/L. Thrombocytopenia is defined as a platelet concentration of less than $150 \times 10^9$/L.

The term "biocompatible" refers to chemical inertness with respect to animal or human tissues or body fluids. Biocompatible materials are non-sensitizing.

The term "compatible linker arm" refers to a moiety which serves to space the oligosaccharide structure from the biocompatible solid support and which is bifunctional wherein one functional group is capable of covalently binding to a reciprocal functional group of the support and the other functional group is capable of binding to a reciprocal functional group of the oligosaccharide structure. Compatible linker arms preferred in the present invention are non-peptidyl linker arms. That is to say that the linker arms do not employ a peptide group to link the oligosaccharide structure to the solid support.

The term "solid support" refers to an inert, solid material to which the oligosaccharide sequences is bound via a compatible linker arm. Where use is in vivo, the solid support will be biocompatible. However, support materials and compounds bound to such materials, which materials are soluble in physiological fluids, are also included.

The solid supports to which the oligosaccharide structures of the present invention are bound may be in the form of particles. A large variety of biocompatible solid support materials are known in the art. Examples thereof are silica, synthetic silicates such as porous glass, biogenic silicates such as diatomaceous earth, silicate-containing minerals such as kaolinite, and synthetic polymers such as polystyrene, polypropylene, and polysaccharides. Solid supports made of inorganic materials are preferred. Preferably the solid supports have a particle size of from about 10 to 500 microns for in vivo use. In particular, particle sizes of 100 to 200 microns are preferred.

The term "SYNSORB" refers to synthetic 8-methoxycarbonyloctyl oligosaccharide structures covalently coupled to CHROMOSORB P™ (Manville Corp., Denver, Colo.) [11], which is a derivatized silica particle.

As used herein, the term "polysaccharide" refers to a moiety with more than one saccharide unit, and includes di- and tri-saccharides.

As used herein, the term "alkyl" refers to monovalent straight, branched or cyclic alkyl groups preferably having from 1 to 20 carbon atoms, more preferably 1 to 10 carbon atoms ("lower alkyl") and most preferably 1 to 6 carbon atoms. This term is exemplified by groups such as methyl, ethyl, n-propyl, iso-propyl, n-butyl, iso-butyl, n-hexyl, and the like. The terms "alkylene" and "lower alkylene" refer to divalent radicals of the corresponding alkane. Further, as used herein, other moieties having names derived from alkanes, such as alkoxyl, alkanoyl, alkenyl, cycloalkenyl, etc when modified by "lower," have carbon chains of ten or less carbon atoms. In those cases where the minimum number of carbons are greater than one, e.g., alkenyl (minimum of two carbons) and cycloalkyl, (minimum of three carbons), it is to be understood that "lower" means at least the minimum number of carbons.

As used herein, the term "substituted alkyl" refers to an alkyl group, preferably of from 1 to 10 carbon atoms ("substituted lower alkyl"), having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino aminoacyl, aminoacyloxy, oxyacylamino, cyano, halogen, hydroxyl, keto, thioketo, carboxyl, carboxylalkyl, thiol, thioalkoxy, substituted thioalkoxy, aryl, aryloxy, heteroaryl, heteroaryloxy, heterocyclic, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and mono- and di-alkylamino, mono- and di-(substituted alkyl)amino, mono- and di-arylamino, mono- and di-heteroarylamino, mono- and di-heterocyclic amino, and unsymmetric di-substituted amines having different substituents selected from the group consisting of alkyl, aryl, heteroaryl and heterocyclic. As used herein, other moieties having the prefix "substituted" are intended to include one or more of the substituents listed above.

As used herein, the term "alkoxy" refers to the group "alkyl-O—", where alkyl is as defined above. Preferred alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

As used herein, the term "alkenyl" refers to alkenyl groups preferably having from 2 to 10 carbon atoms and more preferably 2 to 6 carbon atoms and having at least 1 and preferably from 1–2 sites of alkenyl unsaturation. Preferred alkenyl groups include ethenyl (—CH=CH$_2$), n-propenyl (—CH$_2$ CH=CH$_2$), iso-propenyl (—C(CH$_3$)=CH$_2$), and the like.

As used herein, the term "alkynyl" refers to alkynyl groups preferably having from 2 to 10 carbon atoms and more preferably 2 to 6 carbon atoms and having at least 1 and preferably from 1–2 sites of alkynyl unsaturation.

As used herein, the term "acyl" refers to the groups alkyl-C(O)—, substituted alkyl-C(O)—, cycloalkyl-C(O)—, substituted cycloalkyl-C(O)—, aryl-C(O)—, heteroaryl-C(O)— and heterocyclic-C(O)— where alkyl, substituted alkyl, cycloalkyl, substituted cycloalkyl, aryl, heteroaryl and heterocyclic are as defined herein.

As used herein, the term "acylamino" refers to the group —C(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

As used herein, the term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like. Unless otherwise constrained by the definition for the aryl substituent, such aryl groups can optionally be substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO2-substituted alkyl, —SO2-aryl, —SO2-heteroaryl, trihalomethyl. Preferred substituents include alkyl, alkoxy, halo, cyano, nitro, trihalomethyl, and thioalkoxy.

As used herein, the term "cycloalkyl" refers to cyclic alkyl groups of from 3 to 12 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

As used herein, the terms "halo" or "halogen" refer to fluoro, chloro, bromo and iodo and preferably is either fluoro or chloro.

As used herein, the term "heteroaryl" refers to an aromatic carbocyclic group of from 1 to 15 carbon atoms and 1 to 4 heteroatoms selected from the group consisting of oxygen, nitrogen and sulfur within at least one ring (if there is more than one ring).

Unless otherwise constrained by the definition for the heteroaryl substituent, such heteroaryl groups can be optionally substituted with from 1 to 5 substituents and preferably 1 to 3 substituents selected from the group consisting of acyloxy, hydroxy, acyl, alkyl, alkoxy, alkenyl, alkynyl, substituted alkyl, substituted alkoxy, substituted alkenyl, substituted alkynyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl. Preferred substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). "Heterocycle" or "heterocyclic" refers to a monovalent saturated or unsaturated group having a single ring or multiple condensed rings, from 1 to 15 carbon atoms and from 1 to 4 hetero atoms selected from the group consisting of nitrogen, sulfur or oxygen within the ring.

Unless otherwise constrained by the definition for the heterocyclic substituent, such heterocyclic groups can be optionally substituted with 1 to 5 substituents selected from the group consisting of alkyl, substituted alkyl, alkoxy, substituted alkoxy, aryl, aryloxy, halo, nitro, heteroaryl, thiol, thioalkoxy, substituted thioalkoxy, thioaryloxy, trihalomethyl, and the like. Such heterocyclic groups can have a single ring or multiple condensed rings.

As to any of the above groups that contain 1 or more substituents, it is understood, of course, that such groups do not contain any substitution or substitution patterns which are sterically impractical and/or synthetically non-feasible.

"Pharmaceutically acceptable salts" refers to pharmaceutically acceptable salts of a compound of Formulas IA, IB, or IC, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like can be used as the pharmaceutically acceptable salt.

The term "protecting group" or "blocking group" refers to any group which when bound to one or more hydroxyl, amino or carboxyl groups of the compounds (including intermediates thereof such as the aminolactams, aminolactones, etc.) prevents reactions from occurring at these groups and which protecting group can be removed by conventional chemical or enzymatic steps to reestablish the hydroxyl, amino or carboxyl group. Preferred removable amino blocking groups include conventional substituents such as t-butyoxycarbonyl (t-BOC), benzyloxycarbonyl (CBZ), and the like which can be removed by conventional conditions compatible with the nature of the product.

I. Compounds:

The compounds disclosed herein include a multifunctional core molecule with active sites for coupling to a linker arm, linker arms attached to some or all of the active sites, and bridged dimers or trimers of various di- or tri-saccharides attached to the linker arms via suitable bridging moieties. Suitable compounds are exemplified by the following formula:

$$\text{MFC-(LA)}_n\text{-(BM)}_n$$

where MFC is a multifunctional core molecule, LA is a linker arm, BM is a bridging molecule which includes two or more di-or tri-saccharides, and which can optionally include large oligosaccharides, and n is, independently, between 3 and 20.

The saccharide moieties preferably include the αGal (1→4)βGal subunit and contain at least two 6 sugar units which bind to the shiga-like toxin. Preferably, n is such that the composition contains about 0.25 to 2.50 micromoles oligosaccharide per gram of composition.

A. Multifunctional Core Molecules

As used herein, a suitable multifunctional core molecule is one which is biocompatible, and which includes between three and 20 active sites which can be used to couple with a linker arm. As used herein, "active site" refers to a site which includes a nucleophile or a leaving group such that a linker arm which includes a leaving group or nucleophile, respectively, can be coupled to the core molecule. As an example, a core molecule including a halide can be linked to a linker arm including a hydroxy group via an etherification reaction, or to a linker arm including an amine via nucleophilic displacement of the halide.

Examples of suitable multifunctional core molecules include sugars, such as mono-, di- and tri-saccharides, polyhydroxy compounds such as penta-erithritol, short chain polylysines, polysubstituted aromatics, cycloalkanes, polacrylamides, cyclodextrins, phthalocyanins, mono- and oligosaccharides, inositols, and alditols.

B. Linker Arms

The linker arms are preferably organic bifunctional molecules of appropriate length (at least one carbon atom) which serve simply to distance the oligosaccharide dimers and trimers from the linker arm. Suitable linking arms are described by Lamas et al. [11]. The optimum linker arm length depends on the spatial arrangement of binding sites in the multivalent toxin.

The linker arms are preferably C6-20 straight, branched or cyclic alkanes, in which one or more of the carbons may be replaced with an O, S, or amine. The linker arms can be functionalized at one or more positions with a functional group selected from the group consisting of aryl, substituted aryl, heteroaryl, substituted heteroaryl, heterocyclic and substituted heterocyclic. In order to be coupled to the saccharide moieties, the bridging moiety and the linker arm must include suitable nucleophiles and leaving groups such that they can be coupled together, wherein the groups used to bind the linker arm and bridging moiety are not present in the final compound.

A linker arm is generally between 6 and 20 carbons in length, preferably between 6 and 16 carbons in length, and more preferably, between 6 and 10 carbons in length. The optimum length is determined by x-ray crystallography of the SLT's, which shows the length required for proper orientation of the di- or tri-saccharide moieties to have adequate binding to the SLT. This allows bridged oligomers to simultaneously occupy the adjacent binding sites of toxin subunits and exhibit enhanced affinity relative to monomeric moieties.

The linker arms are bound to a bridging molecule that itself is bound to two or three disaccharides or trisaccharides. Bridged dimers or trimers are linked to between 3 and 20 of the linker arms. However, not all of the linker arms need to be coupled to the bridging molecules for the molecules to be active.

Numerous aglycon linking arms are known in the art. For example, a linking arm comprising a para-nitrophenyl group (i.e., $-OC_6H_4pNO_2$) has been disclosed [29]. At the appropriate time during synthesis, the nitro group is reduced to an amino group which can be protected as N-trifluoroacetamido. Prior to coupling to a support, the trifluoroacetamido group is removed thereby unmasking the amino group.

A linking arm containing sulfur has been disclosed [30]. Specifically, the linking arm is derived from a 2-bromoethyl group which, in a substitution reaction with thionucleophiles, has been shown to lead to linking arms possessing a variety of terminal functional groups such as $-OCH_2CH_2SCH_2CO_2CH_3$ and $-OCH_2CH_2SC_6H_4\text{-}pNH_2$. These terminal functional groups permit reaction to complementary functional groups on the solid support, thereby forming a covalent linkage to the solid support. Such reactions are well known in the art.

A 6-trifluoroacetamido-hexyl linking arm ($-O-(CH_2)_6\text{-NHCOCF}_3$) has been disclosed [31] in which the trifluoroacetamido protecting group can be removed, unmasking the primary amino group used for coupling.

Other exemplifications of known linking arms include the 7-methoxycarbonyl-3,6,dioxaheptyl linking arm [32] ($-OCH_2\text{-}CH_2)_2OCH_2CO_2CH_3$); the 2-(4-methoxycarbonylbutancarboxamido)ethyl [33] ($-OCH_2CH_2NHC(O)(CH_2)_4CO_2CH_3$); the allyl linking arm [34] ($-OCH_2CH=CH_2$) which, by radical co-polymerization with an appropriate monomer, leads to co-polymers; other allyl linking arms [35] are known ($-O(CH_2CH_2O)_2CH_2CH=CH_2$). Additionally, allyl linking arms can be derivatized in the presence of 2-aminoethanethiol [36] to provide for a linking arm $-OCH_2CH_2CH_2SCH_2CH_2NH_2$. Other suitable linking arms have also been disclosed [12–14, 16, 17].

Preferably, the aglycon linking arm is a hydrophobic group and most preferably, the aglycon linking arm is a hydrophobic group selected from the group consisting of $-(CH_2)_8C(O)-$, $-(CH_2)_5OCH_2CH_2CH_2-$ and $-(CH_2)_8CH_2O-$. Non-peptidyl linking arms are preferred for use as the compatible linking arms of the present invention.

The use of glycopeptides is not desirable because glycopeptides contain several, often different, oligosaccharides linked to the same protein. Glycopeptides are also difficult to obtain in large amounts and require expensive and tedious purification. Likewise, the use of BSA or HSA conjugates is not desirable, for example, due to questionable stability in the gastrointestinal tract when given orally.

C. Bridging Molecules

Any molecule which can bind to two or three di-saccharides or tri-saccharides and which can also bind to a linker arm can be used as the bridging molecule. Suitable examples include glycerol, gallic acid and polysubstituted aromatics.

D. Di- and Tri-Saccharides

Suitable di- and tri-saccharides are those which bind to the SLT's, and include those disclosed in U.S. Pat. No. 5,679,653 to Armstrong et al., and also those disclosed in references 3, 46–48, 50–51 and 53.

The compounds preferably include a αGal(1–4)βGal disaccharide subunit which subunit can be used alone or in conjunction with a higher oligosaccharide, e.g., the αGal (1–4)βGal(1–4)βGlcNAc trisaccharide or the αGal(1–4)

βGal(1–4)βGlc trisaccharide. The αGal(1–4)βGal disaccharide subunit is preferably found at the non-reducing terminus of an oligosaccharide. These sugars, and compounds including these sugars, were not found to be particularly active against VT-II toxin, although showed high affinity for VT-I toxin.

Suitable saccharide moieties are those which bind SLTs with relatively high affinity (i.e., a $K_D$ less than about $10^{-3}$ M) and specifically include αGal(1→4)βGal, αGal(1→4)βGal(1→4)βGlcNAc and αGal(1→4)βGal(1→4)βGlc in the form of dimers and/or trimers.

For the purpose of this application, all sugars are referenced using conventional three letter nomenclature. All sugars are assumed to be in the D-form unless otherwise noted, except for fucose, which is in the L-form. Further, all sugars are in the pyranose form.

Between two and three disaccharides and/or trisaccharides of the above saccharides are linked to a bridging molecule as described herein, which bridging molecules are then linked to linker arms, which are then linked to a multifunctional core molecule with between three and 20 sites of attachment.

The saccharide moieties can optionally be functionalized with between one and four functional groups selected from the group consisting of halo, such as fluoro and chloro, thio, carboxy, amine, O-alkyl-S-alkyl, O-alkyl-S-alkyl-C(O)O—, O-alkyl-S-alkyl-S(O)$_2$)—, and guanidine. Saccharides including these substituents are well known to those of skill in the art, and are disclosed, for example, in U.S. Pat. No. 5,679,653 to Armstrong et al., and also those disclosed in references 3, 46–48, 50-51 and 53. Deoxy sugars can also be used, although they will be expected to show less binding affinity. As presented herein, the active saccharides are simple methyl glycosides. However, any simple aglycon, for example, those substitued with (alkyl, aryl, allyl, thioalkyl, and thioaryl, can be used.

In a non-preferred embodiment, additional sugars may be present (i.e., between about 4 and 10 saccharide units), however, the additional saccharide moieties are not expected to assist in the binding to any appreciable extent. Di- and trisaccharides are preferred.

Preferably, the bridging molecule includes a dimer of a tri-saccharide. However, dimers or trimers of trisaccharides, and dimers or trimers of di-saccharides all bind the SLTs with relatively high affinity, provided they are present on a plurality of linker molecules bound to a central core molecule.

II. Pharmaceutical Compositions

Disorders mediated by SLTs can be treated using pharmaceutical compositions that include one or more of the compounds disclosed herein, in combination with a suitable carrier for administration to a patient.

The compositions are preferably administered orally. Preferred compositions for oral administration include pills, tablets, capsules, caplets, syrups, and solutions. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

Compositions which may be mixed with semisolid foods such as applesauce, ice cream or pudding may also be preferred. Formulations, such as SYNSORBs, which do not have a disagreeable taste or aftertaste are preferred. A nasogastric tube may also be used to deliver the compositions directly into the stomach.

Solid compositions may also be used, and may optionally and conveniently be used in formulations containing a pharmaceutically inert carrier, including conventional solid carriers such as lactose, starch, dextrin or magnesium stearate, which are conveniently presented in tablet or capsule form. The SYNSORB itself may also be used without the addition of inert pharmaceutical carriers, particularly for use in capsule form. When a pharmaceutically inert carrier is employed the carrier is typically employed in the amount ranging from about 1 to about 99 percent based on the total weight of the composition and more preferably from about 75 to about 95 weight percent.

Doses are selected to provide neutralization and elimination of SLT toxin and/or elimination of E. coli found in the gut of the affected patient. Preferred doses are from about 0.25 to 1.25 micromoles of oligosaccharide/kg body weight/day, more preferably about 0.5 to 1.0 micromoles of oligosaccharide/kg body weight/day.

Administration of the oligosaccharide-containing compositions during a period of up to seven days will be useful in treating SLT-associated diarrhea and associated conditions.

As discussed previously, oral administration is preferred, but formulations may also be considered for other means of administration, for example, rectal administration. Formulations useful for rectal administration, such as suppositories, are well known to those of skill in the art. The usefulness of these formulations may depend on the particular composition used and the particular subject receiving the treatment. These formulations may contain a liquid carrier that may be oily, aqueous, emulsified or contain certain solvents suitable to the mode of administration.

Compositions may be formulated in unit dose form, or in multiple or subunit doses. For the expected doses set forth previously, orally administered liquid compositions should preferably contain about 1 micromole oligosaccharide/ml.

The compositions can also be administered via injection, i.e., intraveneously, intramuscularly, subcutaneously, intraperitoneally, and intraarterially. Intravenous administration is a preferred method of injection. Suitable carriers for injection are well known to those of skill in the art, and include 5% dextrose solutions, saline, and phosphate buffered saline.

In addition to the carriers disclosed above, the compounds can optionally be covalently attached to or adsorbed onto a biocompatible solid support, e.g., CHROMOSORB P™ (SYNSORB). The bound compounds can be administered to a patient in need of treatment thereof to bind SLT toxins or verotoxins.

When the compounds are bound to a solid support, such as SYNSORB, an effective dosage is about 0.5 to 1.0 gram SYNSORB/kg body weight/day, which gives a concentration of SYNSORB in the gut of about 20 mg/ml. Administration is expected to be 2 to 4 times daily, preferably for a period of one week. The specific dose level and schedule of administration will, of course, vary for each individual depending on factors such as the particular oligosaccharide structure employed, the age and condition of the subject, the extent of the disease condition, all of which are well within the skill of the art.

The compositions are useful to prevent HUS and associated conditions. SYNSORB is particularly preferred for these compositions because it is non-toxic and resistant to mechanical and chemical decomposition. SYNSORBs have been found to pass unaffected through the rat gastrointestinal tract. They were found to be eliminated completely and rapidly (99% eliminated in 72 hours) following oral administration. Additionally, a high density of oligosaccharide moieties can be present on the SYNSORB, which can be particularly useful for binding verotoxins.

III. Compound Preparation

The compounds can be prepared by first selecting a suitable core molecule, suitable linker arms, suitable binding molecules, and suitable di- and/or trisaccharide moieties. The core molecule, which includes a plurality of either nucleophiles or leaving groups, can then be reacted with a plurality of linker arms, which each include a suitable leaving group or nucleophile, respectively, for attachment to the core molecule. Preferably, the linker arms include a protected nucleophile or leaving group at the other end, which, after deprotection, can be used to couple with a suitable binding molecule.

The linker arms, thus bound to the core molecule, are now ready to be coupled with a binding molecule. The binding molecule, previously coupled to two or three di- or trisaccharide moieties using conventional carbohydrate chemistry, also includes a nucleophile or leaving group capable of being reacted with a leaving group or nucleophile, respectively, present on the linker arms.

Chemical methods for the synthesis of oligosaccharide structures, including di- and tri-saccharide moieties, are well known to those of skill in the art. These materials are generally assembled using suitably protected individual monosaccharides.

The di- or trisaccharide structure(s) are covalently bound onto the binding molecule. The covalent bonding may be via reaction between functional groups on the binding molecule and the oligosaccharide structure.

The specific methods employed are generally adapted and optimized for each individual structure to be synthesized. In general, the chemical synthesis of all or part of the oligosaccharide glycosides first involves formation of a glycosidic linkage on the anomeric carbon atom of the reducing sugar or monosaccharide. Specifically, an appropriately protected form of a naturally occurring or of a chemically modified saccharide structure (the glycosyl donor) is selectively modified at the anomeric center of the reducing unit so as to introduce a leaving group comprising halides, trichloroacetimidate, acetyl, thioglycoside, etc. The donor is then reacted under catalytic conditions well known in the art with an aglycon or an appropriate form of a carbohydrate acceptor which possesses one free hydroxyl group at the position where the glycosidic linkage is to be established. A large variety of aglycon moieties are known in the art and can be attached with the proper configuration to the anomeric center of the reducing unit.

Appropriate use of compatible blocking groups, well known in the art of carbohydrate synthesis, will allow selective modification of the synthesized structures or the further attachment of additional sugar units or sugar blocks to the acceptor structures.

After formation of the glycosidic linkage, the saccharide glycoside can be used to effect coupling of additional saccharide unit(s) or chemically modified at selected positions or, after conventional deprotection, used in an enzymatic synthesis. In general, chemical coupling of a naturally occurring or chemically modified saccharide unit to the saccharide glycoside is accomplished by employing established chemistry well documented in the literature [12–28].

IV. Methods of Treatment Using the Compositions

SLT toxin may be neutralized by oligosaccharide sequences comprising the αGal(1→4)βGal subunits which sequences bind the toxin. In particular, the disclosed compounds have been found to neutralize SLT toxin effectively.

The ability of several of the compositions to neutralize SLT toxin has been tested, and the results are shown in FIGS. 3a–d.

The oligosaccharide sequences attached to the core molecule through the binding molecule and the linker arms include those which bind SLT toxin. The binding affinity of an oligosaccharide to SLT toxin is readily detectable by a simple in vitro test, as for example, set forth in Example 1 below. For the purposes of this invention, compounds which bind SLT toxin are those compositions which reduce endpoint titers from cytotoxic activity in vero cell assays by at least 50% and, preferably, by at least 95%, using the assay set forth in the Examples section of U.S. Pat. No. 5,679,653 to Armstrong et al.

The effect of the compositions of the invention in neutralizing SLTs can be measured by comparing activity of the SLT with and without treatment with the compositions. Activity of the SLTs can be assayed by taking advantage of the toxicity of these compounds to Vero cells. Vero cells (ATCC CCL81) can be obtained from the American Type Culture Collection, Rockville Md.

The clinical incidence of HUS arising from enterohemorrhagic *E. coli* infection is reduced when the pharmaceutical compositions described above are administered within 3 days of presentation of the infection and prior to organ involvement other than intestinal involvement. Contrarily, administration of this pharmaceutical composition after this time frame when organs other than the intestine are involved in the infection substantially reduces the ability of this composition to reduce the incidence of HUS.

Preferably, the initial clinical evaluation that the individual is afflicted with an SLT mediated *E. coli* infection is confirmed via diagnostic evaluation of the stool. One diagnostic tool commercially available for detecting SLT mediated *E. coli* infection is sold by Meridian Diagnostic, Inc., Cincinnati, Ohio, USA 45244 under the name Premier EHEC.

Armstrong, et al. [10] established that oligosaccharides comprising a αGal(1→4)βGal subunit possess similar in vitro properties. In vivo results (Armstrong et al., *Eschericia coli* 0157:H7 and other Shiga toxins producing *E. coli* strains, J. B. Caper and A. D. O'Brien, ed. American Society for Microbiology Press, Washington, D.C., 1998) for the $P_k$ trisaccharide have demonstrated the affect of timing of administration of the composition in reducing the incidence of HUS. It is beneficial to administer the compounds to a patient within about three days of infection to have maximal results.

VI. Diagnostic Methods

The compounds can be employed in diagnostic methods which evaluate the presence of enteric *E coli* infection. The diagnostic methods involve the binding of the compounds to the toxins present in the sample, and detecting the bound toxin. The detection can be accomplished using known methodology, for example, by attaching a fluorescent tag or radiolabel to the compound, or by monitoring for changes in various absorbence spectra due to the binding of the toxin and the compound. In one embodiment, the compounds are coupled to or adsorbed onto a solid support, for example, SYNSORB™, and the solid support is then used in a diagnostic assay. Those of skill in the art can readily determine an appropriate set of conditions for evaluating the presence of toxin using the compounds described herein.

As can be appreciated from the disclosure above, the present invention has a wide variety of applications. Accordingly, the following examples are offered by way of illustration and not by way of limitation.

EXAMPLES

In the examples below, all temperatures are given in degrees Celsius and the following abbreviations have the following meanings. If not defined below, then the abbreviations have their art recognized meanings.

ASA=acetylated silylaminated hydrophobic 8-methoxycarbonyloctyl linkage arm
BSA=bovine serum albumin
cm=centimeter
dpm=decays per minute
EDTA=ethylene diamine tetraacetic acid
g=gram
HUS=hemolytic uremic syndrome
kg=kilogram
L=liter
LPS=lipopolysaccharide
M=molar
MEM=minimal Eagles medium
mg=milligrams
mL=milliliters
min.=minutes
mm=millimeters
nm=nanometers
PBS=phosphate buffered saline
pg=picogram
SDS=sodium dodecyl sulfate
SLT=shiga-like toxin
μg=microgram
μL=microliter
μmol=micromol Example 1

General discussion of the Chemistry in Examples 2–18

A general approach to the preparation of $P^k$ trisaccharide analogues modified at the C-2 position of the central galactose residue was developed, as shown in FIG. 1*a–d*. Compound 22 appears to be the most preferred compound. Since the VTI toxin is a pentamer, and bridged dimers of di- and tri-saccharides are known to bind to the toxin, the compound was designed to be a pentamer with bridged dimers of di- and tri-saccharides such that the compound could most effectively bind to the toxin.

The known lactose derivative 1 was allylated; the product was subjected to acid hydrolysis and acetylation to give a mixture of anomeric heptaacetates 2. Conversion of 2 into lactosyl chloride 3 was achieved by a treatment with dichloromethyl methyl ether in the presence of $ZnBr_2$. Glycosidation of chloride 3 by methanol with concurrent removal of acetates led to the selectively allylated methyl β-lactoside 4. Acid catalyzed reaction of the lactoside 4 with α,α-dimethoxytoluene gave the 4',6'-O-benzylidene derivative 5, which was perbenzylated to afford 6. Acid hydrolysis of 6 followed by selective benzoylation of the primary hydroxyl in diol 7 with BzC1 in pyridine afforded the glycosyl acceptor 8, that was glycosylated with chloride 9 in toluene in the presence of AgOTf and a hindered base to give trisaccharide 10. Replacement of the 6'-O-benzoyl group by a benzyl group provided the trisaccharide 12 conveniently protected with temporary (allyl) and "permanent" (benzyl) protecting groups. Oxidation of the double bond with 4-methylmorpholine N-oxide in the presence of $OsO_4$ followed by $NaIO_4$ cleavage of the formed diol led to an aldehyde (which can be isolated) which was reduced to alcohol 13 by the treatment of the reaction mixture with excess of $NaBH_4$ (one pot transformation from 12). The resulting alcohol 13 was esterified by p-nitrophenyl chloroformate in pyridine to give the p-nitrophenyl carbonate 14. Reaction of 14 with 0.5 eq. of 1,3-diamino-2-hydroxypropane in THF provided the bridged trisaccharide dimer 15. Esterification of the secondary alcohol in the same manner described for compound 13 gave the activated carbonate 16, which upon condensation with an excess of 1,8-diaminooctane formed 17. Hydrogenation of 17 gave the target bridged $p^k$ cluster with amine terminated linker 18. The amino group of the spacer arm was activated as a squaric acid derivative 19. This activated derivative of the trisaccharide dimer was linked to a five-fold scaffold made from a functionalized glucose molecule 21 to give a pentameric presentation of trisaccharide dimers (compound 22). Compound 22 is also referred to herein as "starfish".

In the Examples to follow, NMR spectra refer to assignments of various hydrogens in various positions on the compounds. The following structure shows the numbering scheme for the compounds.

Coupling Constants and Ring Numbering

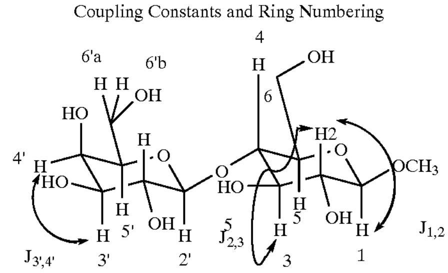

Example 2

Preparation of 1,2,3,6-Tetra-O-acetyl-4-O-(3,4,6-tri-O-acetyl-2-O-allyl-β-D-galactopyranosyl)-α,β-D-glucopyranose (2)

A solution of 1 (6.81 g, 11.7 mmol), NaH (95%, 0.885 g, 35.2 mmol), and allyl bromide (2.03 mL, 23.4 mmol) was refluxed for 3 h until alkylation was complete, then MeOH was added and the mixture was neutralized with acetic acid (HOAc). The mixture was filtered through Celite and the filtrate was concentrated. The residue was dissolved in 60% HOAc, refluxed for 2 h, and concentrated. The residue was crystallized from EtOH, the crystals were collected and dried in a desiccator over $P_2O_5$. A mixture of the residue in pyridine (30 ml) and $Ac_2O$ (30 ml) was stirred at 60° C. for 1 h under an Ar atmosphere. The mixture was concentrated, co-evaporated three times with toluene and the residue was chromatographed on silica gel with pentane-EtOAc (7:3) to give 2 (5.79 g, 73%); $^1H$ NMR ($CDCl_3$) δ 6.26 (d, $J_{1,2}$=3.7 Hz, H-1α), 5.78 (Hc), 5.68 (d, $J_{1,2}$=8.3 Hz, H-1β), 5.44 (dd, J=9.3 Hz, J=10.2 Hz, H-3α). Calc'd for $C_{29}H_{40}O_{18}$ (676.62) C, 51.48; H, 5.96. Found C, 51.38; H, 5.84.

Example 3

Preparation of 2,3,6-Tri-O-acetyl-4-O-(3,4,6-tri-O-acetyl-2-O-allyl-β-D-galactopyranosyl)-α-D-glucopyranosyl choride (3)

To a solution of 2 (3.5 g, 5.17 mmol) in $CH_2Cl_2$ (10 mL) $Cl_2CHOCH_3$ (0.56 mL, 6.2 mmol) and $ZnBr_2$ (100 mg) were added under an Ar atmosphere. The mixture was stirred for 1 h, then concentrated and the residue was chromatographed on silica gel with pentane-EtOAc (6:4) to give 3 (396 mg, 85%), $[\alpha]_D$+93.4° (c 1.2, $CHCl_3$); $^1H$ NMR ($CDCl_3$) δ 6.22 (s, 1H, $J_{1,2}$=3.9 Hz, H-1), 5.80 (m, 1H, Hc), 5.56 (t, 1H, $J_{3,4}$ and $J_{2,3}$≈9.7 Hz, H-3), 5.31 (dd, 1H, $J_{4',3'}$=3.5 Hz, $J_{4',5'}$=0.8

Hz, H-4'), 5.20 (1H, Hb), 5.12 (1H, Ha), 4.93 (dd, 1H, H-2), 4.86 (dd, 1H, $J_{2',3'}$=10.2 Hz, H-3'), 4.58 (dd, 1H, $J_{6a,6b}$=12.1 Hz, $J_{5,6a}$=0.7 Hz, H-6a), 4.34 (d, 1H, $J_{1',2'}$=7.7 Hz, H-1'), 4.29 (dd, 1H, $J_{5,6b}$=4.2 Hz, H-6B), 4.25–4.01 (m, 5H, Hd, He, H-5, H-6'a, H-6'b), 3.85–3.78 (m, 2H, H-4, H-5'), 3.42 (dd, 1H, H-2'). Calc'd for $C_{27}H_{37}ClO_{16}$ (653.025) C, 49.66; H, 5.71, Cl, 5.43. Found C, 49.68, H, 5.68, Cl, 5.73.

Example 4

Preparation of Methyl 4-O-(2-O-allyl-β-D-galactopyranosyl)-β-D-glucopyranoside (4)

Chloride 3 (4.4 g, 6.74 mmol) was dissolved in dry MeOH and left at room temperature for two days. The mixture was neutralized with Dowex 50W (H+) resin, the suspension was filtered and the filtrate was crystallized from EtOH to give 4 (1.8 g, 67%), $[\alpha]_D$–1.8° (c 0.2, $H_2O$), m.p. 22–223° C.; $^1H$ NMR ($D_2O$) δ 5.99 (m, 1H, Hc), 5.36 (m, 1H, Hb), 5.28 (m, 1H, Ha), 4.49 (d, 1H, $J_{1',2'}$=7.9 Hz, H-1'), 4.41 (d, 1H, $J_{1,2}$=8.0 Hz, H-1), 4.34 (m, 1H, Hd), 4.26 (m, 1H, He), 3.99 (broad d, 1H, H-6a), 3.83–3.62 (m, 8H, H-3, H-4, H-5, H-6b, H-3', H-5', H-6', H-6'b), 3.58 (s, 3H, Me), 3.4dd, 1H, $J_{2',3'}$=10.0 Hz, H-2'), 3.32 (m, H-2). Calc'd for $C_{16}H_{28}O_{11}$ (396.38) C, 48.48; H, 7.12. Found C, 48.47, H, 7.12.

Example 5

Preparation of Methyl 4-O-(2-O-allyl-4,6-O-benzylidine-β-D-galactopyranosyl)-β-D-glucopyranoside (5)

Methyl β-lactoside 4 (1.56 g, 3.93 mmol) was lyophilised from water (20 mL). To a mixture of the residue and α,α-dimethoxytoluene (1.2 mL, 2 eq.) in dry MeCN (15 mL) toluenesulfonic acid (150 mg) was added. The mixture was refluxed for 3 min then neutralized with pyridine and concentrated. Chromatography of the residue on silica gel with methylene chloride-MeOH (20:1) gave 5 (1.25 g, 64%), $[\alpha]_D$–23.1° (c 0.4, MeOH), m.p. 212–213° C.; $^1H$ NMR ($CH_3OD$) δ 7.55–7.33 (m, 5H, arom), 5.96 (m, 1H, Hc), 5.63 (s, 1H, CHPh), 5.27 (m, 1H, Hb), 5.12 (m, 1H, Ha), 4.52 (d, 1H, $J_{1',2'}$=7.8 Hz, H-1'), 4.29–4.12 (m, 6H, Hd, He, H-1, H-4', H-6'a, H-6'b), 3.88 (m, 2H, H-6a, H-6b), 3.70 (dd, 1H, $J_{3',4'}$=3.6 Hz, $J_{2',3'}$=9.7 Hz, H-3'), 3.62–3.54 (m, 3H, H-3, H-4, H-5'), 3.52 (s, 3H, Me), 3.45 (dd, 1H, H-2'), 3.42–3.37 (m, 1H, H-5), 3.23 (m, H-2). Calc'd for $C_{23}H_{32}O_{11}$ (484.49) C, 57.02; H, 6.66. Found C, 56.82, H, 6.66.

Example 6

Preparation of Methyl 4-O-(2-O-allyl-3-O-benzyl-4,6-O-benzylidine-β-D-galactopyranosyl)-2,3,6-tri-O-benzyl-β-D-glucopyranoside (6)

A mixture of 5 (780 mg, 1.79 mmol) and 95% NaH (235 mg, 9.33 mmol) in dry DMF (5mL) BnBr (1.1 mL, 9.33 mmol) was added. After 1 h the reaction was quenched with MeOH and the mixture was diluted with EtOAc. The solution was washed with brine, and then concentrated. Chromatography of the residue on silica gel with hexane-EtOAc (7:3) gave 6 (1.35 g, 89%), $[\alpha]_D$+23.0° (c 0.26, $CHCl_3$), m.p. 128–129° C.; $^1H$ NMR ($CDCl_3$) δ 7.50–7.12 (m, 25H, arom), 5.91 (m, 1H, Hc), 5.42 (s, 1H, CHPh), 5.24 (1H, Hb), 5.13 (d, 1H, $^2J$=10.5 Hz, Bn), 5.11 (1H, Ha), 4.86 (d, 1H, $^2J$=11.0 Hz, Bn), 4.41 (d, 1H, $J_{1',2'}$=7.8 Hz, H-1'), 4.29 (d, 1H, $J_{1,2}$=7.8 Hz, H-1), 4.29–4.19 (m, 2H, Hd, He), 4.15 (dd, 1H, $J_{6'a,6'b}$=12.2 Hz, $J_{5',6'a}$<1 Hz, H-6'a), 4.02–4.92 (m, 3H, H-4, H-6a, H-4'), 3.84 (dd, 1H, $J_{6b,6a}$=9.5 Hz, $J_{5,6b}$=1.4 Hz, H-6b), 3.80 (dd, 1H, $J_{5',6'b}$=1.8 Hz, H-6'b), 3.63–3.55 (m, 2H, H-2', H-3), 3.55 (s, 3H, Me), 3.44–3.38 (m, 2H, H-2, H-5), 3.28 (dd, 1H, $J_{3',4'}$=3.7 Hz, $J_{2',3'}$=9.6 Hz, H-3'), 2.85 (broad s, 1H, H-5'), 2.35 (broad s, 1H, OH). Calc'd for $C_{51}H_{56}O_{11}$ (844.98) C, 72.49; H, 6.68. Found C, 72.41, H, 6.62.

Example 7

Preparation of Methyl 4-O-(2-O-allyl-3-O-benzyl-β-D-galactopyranosyl)-2,3,6-tri-O-benzyl-β-D-glucopyranoside (7)

Disaccharide 6 (2.13 g, 2.52 mmol) was dissolved in aqueous 80% acetic acid (30 mL) and stirred at 80° C. for 2 h. Then solvents were evaporated, co-evaporated with toluene (3×) and the residue was chromatographed on silica gel with hexane- EtOAc (4:1) to give 7 (1.6 g, 85.6%), $[\alpha]_D$+31.0° (c 0.6, $CHCl_3$), m.p. 119–120° C.; $^1H$ NMR ($CDCl_3$) δ 7.20–7.10 (m, 20H, arom), 5.90 (1H, Hc), 5.25 (1H, Hb), 5.13 (1H, Ha), 4.97 (d, 1H, $^2J$=10.9 Hz, Bn), 4.87 (d, 1H, $^2J$=11.0 Hz, Bn), 4.77 (d, 1H, $^2J$=10.9 Hz, Bn), 4.72 (d, 1H, $^2J$=11.1 Hz, Bn), 4.68 (s, 2H, Bn), 4.66 (d, $^2J$=12.1 Hz, Bn), 4.50 (d, $^2J$=12.1 Hz, Bn), 4.34 (d, 1H, $J_{1',2'}$=7.9 Hz, H-1'), 4.30 (d, 1H, $J_{1,2}$=7.8 Hz, H-1), 4.30–4.18 (m, 2H, Hc, Hd), 3.95–3.80 (m, 4H, H-4, H-6a, H-6b, H-4'), 3.62–3.38 (m, 9H, H-2, H-3, H-5, H2', H-6'a, H-6'b, Me), 3.24 (dd, 1H, $J_{2',3'}$=9.3 Hz, $J_{3',4'}$=3.4 Hz, H-3'), 3.09 (m, 1H, H-5'), 2.58 (d, 1H, $J_{4',OH}$=1.9 Hz, 4'-OH), 2.02 (dd, 1H, $J_{6'a, OH}$=4.7 Hz, $J_{6'b, OH}$=8.3 Hz, 6'OH). Calc'd for $C_{44}H_{52}O_{11}$ (756.87) C, 69.82; H, 6.92. Found C, 69.78 H, 7.00.

Example 8

Preparation of Methyl 4-O-(2-O-allyl-3-O-benzyl-6-O-benzoyl-β-D-galactopyranosyl)-2,3,6-tri-O-benzyl-β-D-glucopyranoside (8)

To solution of 7(1.53 g, 2.024 mmol) in dry pyridine (10 mL) benzoyl chloride (0.235 mL, 2.024 mmol) was added dropwise at 0° C. under argon atmosphere. After 3 h a few drops of water were added to the mixture and all solvents were evaporated. Chromatography of the residue on silica gel with hexane-EtOAc (4:1) gave 8 (1.57 g, 90.2%), $[\alpha]_D$+19.70 (c 0.6, $CHCl_3$); $^1H$ NMR ($CDCl_3$) δ 8.00–7.98 (m, 2H, Bz), 7.58–7.13 (m, 23H, arom), 5.90 (m, 1H, Hc), 5.24 (m, 1H, Hb), 5.13 (m, 1H, Ha), 4.98 (d, 1H, $^2J$=10.8 Hz, Bn), 4.84 (d, 1H, $^2J$=11.0 Hz, Bn), 4.76–4.64 (m, 5H, Bn), 4.48 (dd, 1H, $J_{5',6'a}$=6.6 Hz, $J_{6'a,6'b}$=11.2 Hz, H-6'a), 4.46 (d, 1H, $^2J$=12.1 Hz, Bn), 4.39 (d, 1H, $J_{1',2'}$=7.8 Hz, H-1'), 4.28 (d, 1H, $J_{1,2}$=7.7 Hz, H-1), 4.28–4.16 (m, 3H, Hd, He, H-6'b), 3.98 (t, 1H, $J_{3,4}$–$J_{4,5}$=9.1 Hz, H-4), 3.91 (dd, 1H, $J_{5,6a}$=4.0 Hz), $J_{6a,6b}$=10.9 Hz, H-6a), 3.84–3.78 (m, 2H, H-4', H-6b), 3.58 (t, 1H, $J_{2,3}$=9.1 Hz, H-3), 3.54 (s, 3H, Me), 3.46–3.33 (m, 4H, H-2, H-2', H-5, H-5'), 3.26 (dd, 1H, $J_{2',3'}$=9.3 Hz, $J_{3',4'}$=3.5 Hz, H-3'). Calc'd for $C_{51}H_{56}O_{12}$ (860.98) C, 71.14; H, 6.56. Found C, 70.98 H, 6.68.

Example 9

Preparation of Methyl 4-O-[(2-O-allyl-3-O-benzyl-4-O-(2,3,4,6-tetra-O-benzyl-α-D-galactopyranosyl)-β-D-galactopyranosyl]-2,3,6-tri-O-benzyl-β-D-glucopyranoside (11)

A solution of freshly prepared 2,3,4,6 -tetra-O-benzyl-α-D-galactopyranosyl-chloride 9 (5.63 g, 10.07 mmol) in dry toluene (30mL) was added dropwise to a stirred solution of 8 (5.45 g, 6.34 mmol), silver triflate (3.08 g, 12 mmol) and 2,4,6-collidine (1.6 mL, 12 mmol) in dry toluene (100 mL) at −40° C. The reaction mixture was allowed to warm to room temperature. After 2 h the mixture was transferred into a separatory funnel, washed with a solution of $Na_2S_2O_3$ and extracted with toluene. All solvents were evaporated and the crude product was used for the next step without purification. The product 10 was treated with a catalytic amount of NaOMe in MeOH-THF at room temperature overnight until the benzoyl group was removed. The reaction mixture was neutralized with acetic acid, concentrated, taken up into $CH_2Cl_2$, washed with water and concentrated. Column chromatography (hexane-EtOAc, 4:1) of the residue yielded 11 (6.02 g, 74.3%), $[\alpha]_D$+29.7° (c 1.2, $CHCl_3$); $^1H$ NMR ($CDCl_3$) δ 7.35–7.10 (m, 40H, arom), 5.82 (1H, Hc), 5.16 (1H, Hb), 5.08–5.03 (M, 2H, Ha, Bn), 4.96 (d, 1H, $J_{1'',2''}$=3.3 Hz, H-1''), 4.86–4.78 (m, 3H, Bn), 4.69–4.43 (m, 10H, Bn), 4.37 (d, 1H, $J_{1',2'}$=7.7 Hz, H-1'), 4.31–4.21 (m, 3H, H-1, Bn), 4,15–4.08 (m, 3H, H-5'', Hc, Hd), 4.02 (dd, 1H, $J_{2'',3''}$=10.1 Hz, H-2''), 3.93–3.79 (m, 6H, H-4, H-6a, H-6b, H-4', H-3'', H-4''), 3.70–3.57 (m, 2H, H-6'a, H-6'b), 3.54 (s, 3H, Me), 3.53 (t, 1H, $J_{3,2}$–$J_{3,4}$=9.0 Hz, H-3), 3.45–3.32 (m, 4H, H-2, H-5, H-2'',H-6''a), 3.28 (dd, 1H, $J_{6''b,6''a}$=8.9 Hz, $J_{5'',6''b}$=5.4 Hz, H-6''b), 3.22–3.16 (m, 2H, H-3', H-5'). Calc'd for $C_{78}H_{86}O_{16}$ (1279.508) C, 73.22; H, 6.77. Found C, 73.29 H, 6.86.

Example 10

Preparation of Methyl 4-O-[(2-O-allyl-3,6-di-O-benzyl-4-O-(2,3,4,6-tetra-O-benzyl-α-D-galactopyranosyl)-β-D-pyranosyl]-2,3,6-tri-O-benzyl-β-D-glucopyranoside (12)

Benzyl bromide (0.84 ml, 7.07 mmol) was added with stirring to a solution of 11 (6.02 g, 4.71 mmol) in DMF (50 ml) containing suspension of 95% NaH (180 mg, 7.07 mmol) at room temperature. After 3 h excess sodium hydride was decomposed by adding a few drops of methanol. Solvents were evaporated, the residue was dissolved in EtOAc, the solution was washed with brine and concentrated. Column chromatography (hexane-EtOAc, 9:1) of the residue yielded 12 (5.4 g, 83.8%), $[\alpha]_D$+34.2° (c 0.9, $CHCl_3$); $^1H$ NMR ($CDCl_3$) δ 7.38–7.10 (m, 45H, arom), 5.91 (1H, Hc), 5.23 (1H, Hb), 5.11 (1H, Ha), 5.05–5.00 (m, 2H, H-1'', Bn), 4.83 (d, 1H, $^2J$=11.2 Hz, Bn), 4.81 (d, 1H, $^2J$=11.0 Hz, Bn), 4.75–4.62 (m, 6H, Bn), 4.52–4.40 (m, 6H, H-1', Bn), 4.34–3.89 (m, 10H, H-1, H-4, H-6a, H-4', H-6'a, H-2'', H-3'', H-4'', H5'', Bn, Hd, He), 3.83 (dd, 1H, $J_{5,6b}$=1.5 Hz, $J_{6a,6b}$=10.8 Hz, H-6b), 3.55 (t, 1H, $J_{3,2}$–$J_{3,4}$=8.0 Hz, H-3), 3.53 (s, 3H, Me), 3.50–3.38 (m, 4H, H-5, H-2', H-6'b, H-6''a), 3.35 (dd, 1H, $J_{2,1}$=7.9 Hz, $J_{2,3}$=9.1 Hz, H-2), 3.24 (dd, 1H, $J_{3',4'}$=5.3 Hz, $J_{2',3'}$=8.4 Hz, H-3'), 3.19 (dd, 1H, $J_{5',6'a}$=2.7 Hz, $J_{5',6'b}$=10.0 Hz, H-5'), 3.12 (dd, 1H, $J_{5'',6''b}$=4.6 Hz, $J_{6''a, 6''b}$=8.2 Hz, H-6''b). Calc'd for $C_{85}H_{92}O_{16}$ (1369.63) C, 74.54; H, 6.77. Found C, 74.36 H, 6.77.

Example 11

Preparation of Methyl 4-O-[3,6-di-O-benzyl-4-O-(2,3,4,6-tetra-O-benzyl-α-D-galactopyranosyl)-2-O-(2-hydroxyethyl)-β-D-galactopyranosyl-2,3,6-tri-O-benzyl-β-D-glucopyranoside (13)

A mixture of 12 (570 mg, 0.411 mmol), 4-methylmorpholine N-oxide (96 mg, 2 eq), and $OsO_4$ (0.5 mL, 1M t-BuOH solution) in acetone (10 mL) and water (1 mL) was stirred for 3 days, then concentrated, taken up in $CH_2Cl_2$, washed with water, and concentrated again. The residue was dissolved in THF (15 ml) and water (5 mL) and $NaIO_4$ (174 mg, 2 eq) was added. After 3 h at 50° C. $NaBH_4$ (110 mg, 7 eq) was added. The mixture was neutralized with 1N HCl, diluted with water, and extracted with $CH_2Cl_2$ Chromatography of the residue on silica gel with pentane—ethyl acetate (65:35) gave 13 (490 mg, 87%), $[\alpha]_D$+36.1 ° (c 0.26, $CHCl_3$); $^1H$ NMR ($CDCl_3$) δ 7.4–7.1 (m, 45H, arom), 5.02–4.99 (m, 2H, H-1'', Bn), 4.83–4.62 (m, 8H, Bn), 4.50–4.32 (m, 6H, H-1', Bn), 4.28–4.09 (m, 7H, H-1, H-4', H-5'', Bn), 4.04 (dd, 1H, $J_{1'',2''}$=3.3 Hz, $J_{2'',3''}$=10.3 Hz, H-2''), 4.02–3.70 (m, 8H, H-4, H-6a, H-6b, H-5', H-3'', H-4'', $CH_2$), 3.52 (s, 3H, Me), 3.62–3.35 (m, 7H, H-3, H-5, H-2', H-6'a, H-6''a, $CH_2$), 3.33 (dd, 1H, $J_{1,2}$=7.7 Hz, $J_{2,3}$=9.0 Hz, H-2), 3.27–3.12 (m, 3H, H-3', H-6'b, H-6''b). Calc'd for $C_{84}H_{92}O_{17}$ (1373.62) C, 73.45; H, 6.75. Found C, 73.48, H, 6.74.

Example 12

Preparation of Methyl 4-O-[3,6-di-O-benzyl-4-O-(2,3,4,6-tetra-O-benzyl-α-D-galactopyranosyl)-2-O-(2-(4-nitrophenyloxy)ethyl)-p-D-galactopyranosyl]-2,3,6-tri-O-benzyl-β-D-glucopyranoside (14)

A mixture of 13 (434 mg, 0.316 mmol), 4-nitrophenyl chloroformate (74 mg, 1.2 eq.) in dry pyridine (3 mL) was stirred for 4 h at 50° C., then the reaction was quenched with a droplet of water, concentrated and chromatographed on silica gel with pentane—ethyl acetate (80:20–75:25) to give 14 (406 mg, 85%), $[\alpha]_D$+29° (c 0.5, $CHCl_3$); $^1H$ NMR ($CDCl_3$) δ 8.17 (m, 2H, arom), 7.40–7.10 (m, 47H, arom), 5.02–5.00 (m, 2H, H-1'', Bn), 4.85–4.62 (m, 8H, Bn), 4.50–4.40 (m, 6H, H-1', Bn), 4.32–4.20 (m, 6H, H-1, H-4', $CH_2$, Bn), 4.15–3.82 (m, 12H, H-4, H-6a, H-6b, H-5', H-2'', H-3'', H-4'', H-5'', $CH_2$, Bn), 3.54 (t, 1H, $J_{2,3}$–$J_{3,4}$=9.0 Hz, H-3), 3.50 (s, 3H, Me), 3.50–3.40, (m, 4H, H-5, H-2', H-6'a, H-6''a), 3.34 (dd, 1H, $J_{1,2}$=7.8 Hz, H-2), 3.29–3.20 (m, 2H, H-6'b, H-6''b,), 3.16 (dd, 1H, $J_{2',3'}$=8.4 Hz, $J_{3',4'}$=4.7 Hz, H-3'). Calc'd for $C_{91}H_{95}NO_{21}$ (1538.72) C, 71.03; H, 6.22, N, 0.91. Found C, 71.03, H, 6.29, N, 0.91.

Example 13

Preparation of N,N'-Bis{2-[methyl 4-O-(3,6-di-O-benzyl-4-O-(2,3,4,6-tetra-O-benzyl-α-D-galactopyranosyl)-⊖-D-galactopyranosyl)-2,3,6-tri-O-benzyl-β-D-glucopyranoside 2'-yloxy]-ethoxycarbonyl}-1,3-diamino-2-hydroxypropane (15)

A solution of 14 (643 mg, 0.418 mmol) and 1,3-diamino-2-hydroxypropane (18.8 mg, 0.209 mmol) in THF (10 mL) was stirred overnight at room temperature. The mixture was concentrated and chromatographed on silica gel in hexane—ethyl acetate (7: 3, then 3: 2) to give 15 (554 mg, 92.3%), $[\alpha]_D$+27.2° (c 0.6, $CHCl_3$); $^1H$ NMR ($CDCl_3$) δ 7.4–7.1 (m, 90H, arom), 5.72 (m, 2H, NH), 5.05–5.00 (m, 4H, H-1'', Bn), 4.82 (d, 2H, $^2J$=11.3 Hz, Bn), 4.79 (d, 2H, $^2J$=11.0 Hz, Bn), 4.74–4.60 (m, 16H, $OCH_2$, Bn), 4.50–4.24 (m, 22H, H-1, H-1', H-4', Bn), 4.13–3.73 (m, 26H, H-4, H-6a, H-6b, H-5', H-6'a, H-2'', H-3'', H-4'', H-5'', $OCH_2$, Bn), 3.52 (t, 2H, $J_{2,3}$–$J_{3,4}$=9.1 Hz, H-3), 3.51 (s, 6H, Me), 3.50–3.22 (m, 13H, H-2, H-5, H-2', H-6'b, H-6''a, H-6''b, $CHCH_2N$), 3.13 (dd, 2H, $J_{2',3'}$=8.1 Hz, $J_{3',4'}$=4.7 Hz, H-3'), 2.90–2.60 (m, 4H, $CH_2N$). Calc'd for $C_{173}H_{190}N_2O_{37}$ (2889.35) C, 71.91; H, 6.63, N, 0.97. Found C, 71.82, H, 6.71, N, 0.95.

Example 14

Preparation of N,N-Bis{2-[methyl 4-O-(3,6-di-O-benzyl-4-O-(2,3,4,6-tetra-O-benzyl-α-D-galactopyranosyl)-β-D-galactopyranosyl)-2,3,6-tri-O-benzyl-β-D-glucopyranoside 2'-yl oxy]-ethoxycarbonyl}-1,3-diamino-2-hydroxypropane p-nitrophenylcarbonate (16)

A solution of 15 (552 mg, 0.191 mmol) and 4-nitrophenyl chloroformate (46 mg, 0.228 mmol) in dry pyridine was stirred overnight at 30° C. Pyridine was removed by evaporation and co-evaporation with toluene twice. Chromatography of the residue on silica gel with pentane—ethyl acetate (80:20, 60:40) gave 16 (374 mg, 75%), $[\alpha]_D$+33.6° (c 0.6, CHCl$_3$); $^1$H NMR (CDCl$_3$) δ 8.1 (d, 2H, $^3$J=9.0 Hz), 7.4–7.1 (m, 92H, arom), 5.93 (m, 2H, NH), 5.05–5.00 (m, 4H, H-1", Bn), 4.82 (d, 2H, $^2$J=11.9 Hz, Bn), 4.77–4.56 (m, 16H, Bn), 4.49–4.24 (m, 20H, H-1, H-4', Bn), 4.13–3.73 (m, 25H, H-4, H-6a, H-6b, H-5', H-2", H-3", H-4", H-5", OCH$_2$, CHCH$_2$N, Bn), 3.52 (t, 2H, J$_{2,3}$-J$_{3,4}$=9.0 Hz, H-3), 3.51 (s, 6H, Me), 3.49–3.21 (m, 14H, H-2, H-5, H-6'a, H-6'b, H-6"a, H-6"b, CH$_2$O), 3.12 (dd, 2H, J$_{2',3'}$=8.2 Hz, J$_{3',4'}$=4.7 Hz, H-3'), 2.81–2.66 (m, 2H, CH$_2$N). Calc'd for C$_{180}$H$_{193}$N$_3$O$_{41}$ (3054.45) C, 70.78; H, 6.37, N, 1.38. Found C, 70.74 H, 6.34, N, 1.36.

Example 15

Preparation of N,N'-Bis{2-[methyl 4-O-(3,6-di-O-benzyl-4-O-(2,3,4,6-tetra-O-benzyl-α-D-galactopyranosyl)-β-D-galactopyranosyl)-2,3,6-tri-O-benzyl-β-D-glucopyranoside 2'-yloxy]-ethoxycarbonyl}-1,3-diamino-2-(8-aminooctyl) carbamoyloxy-propane (17)

A solution of 16 (350 mg, 0.115 mmol) in THF (2 ml) was added dropwise to a solution of 1,8-diaminooctane (315 mg, 1.49 mmol) in THF (1.5 ml). After 15 min TLC (CH$_2$Cl$_2$: MeOH, 10:1) indicated that the reaction was completed. Concentration of the reaction mixture and column chromatography of the residue on silica gel with CH$_2$Cl$_2$: MeOH: 30%NH$_3$ (10: 1: 0.1) gave 17 (348 mg, 98%), $[\alpha]_D$+28.6° (c 0.6; CHCl$_3$); $^1$H NMR (CH$_3$OD-CDCl$_3$) δ 7.4–7.1 (m, 90H, arom), 5.09 (d, 2H, $^2$J=11.0 Hz, Bn), 5.04 (d, 2H, J$_{1",2"}$=2.4 Hz, H-1"), 4.8–4.55 (m, 16H, Bn), 4.52–4.03 (m, 32H, H-1, H-1', CHCH$_2$N, CH$_2$NHCO, CH$_2$O, Bn), 3.96–3.78 (m, 20H, H-4, H-6a, H-6b, H-4', H-6'a, H-2", H-3", H-4", CH$_2$O), 3.61 (ddd, 2H, J=6.1 Hz, J=9.8 Hz, J$_{4',5'}$<1 Hz, H-5'), 3.51 (s, 6H, OMe), 3.54–3.06 (m, 20H, H-2, H-3, H-5, H-2', H-3', H-5', H-6'b, H-6"a, H-6"b, CH$_2$N), 3.00–2.95 (m, 2H, CH$_2$N), 2.79 (t, 2H, $^3$J=7.6 Hz, CH$_2$NH$_2$), 1.67 (p, 2H, $^3$J=6.2 Hz, CH$_2$CH$_2$NHCO), 1.57–1.52 (m, 1H, CH$_2$CH$_2$NH$_2$), 1.46–1.20 (m, 7H, CH$_2$), 0.90–0.83 (m, 2H, CH$_2$). Calc'd for C$_{182}$H$_{208}$N$_4$O$_{38}$ (3059.60) C, 71.45; H, 6.85, N, 1.83. Found C, 71.36 H, 6.91, N, 1.63.

Example 16

Preparation of N,N'-Bis{2-[methyl 4-O-(4-O-(α-D-galactopyranosyl)-β-D-galactopyranosyl)-β-D-glucopyranoside 2'-yloxy]-ethoxycarbonyl}-1,3-diamino-2-(8-ammomiooctyl)carbamoyloxy-propane acetate (18)

A solution of 17 (350 mg, 0.114 mmol) in HOAc (10 ml) was hydrogenated in the presence of 10% Pd/C (20 mg). The mixture was filtered and concentrated, and a solution of the residue in water was passed through Sep-Pak (C- 18) to give 18 (125 mg, 69%), $[\alpha]_D$+38.2°(c 0.17; H$_2$O) $^1$H-NMR δ 4.92 (d, 2H, J$_{1",2"}$=3.5 Hz, H-1"), 4.48 (m, 4 lines, 2H, H-1'), 4.37–4.29 (m, 4H, H-1, H-5"), 4.22–4.16 (m, 4H, H-4', H-4"), 4.10–3.50 (m, broad lines), 3.54 (s, 6H, OMe), 3.37 (broad t, 2H, J$_{2',3'}$=9.1 Hz, H-2'), 3.26 (broad t, 2H, J$_{2,3}$=8.2 Hz, H-2), 3.06 (t, 2H, $^3$J=6.7 Hz, C(O)NHCH$_3$), 2.95 (t, $^3$J=7.6 Hz, CH$_3$NH$_2$), 1.87 (s, 3H, Ac), 1.63 (m, 2H, CH$_2$ CH$_2$ NH$_2$), 1.50–1.20 (m, 10H, CH$_2$). Electrospray ionisation MS: 1437.6133 (Calcd. for C$_{56}$H$_{101}$N$_4$O$_{38}$ 1437.6094).

Example 17

Preparation of N,N'-Bis{2-[methyl 4-O-(4-O-(α-D-galactopyranosyl)-β-D-galactopyranosyl)-β-D-glucopyranoside 2'-yloxyl-ethoxycarbonyl}-1,3-diamino-2-[8-(4-ethoxy-2,3-dioxo-3-cyclobutenylamino)octyl]carbamoyloxy-propane (19)

To a solution of 18 (30.8 mg, 20.5 μmol) in 1 mL of MeOH 3,4-diethoxy-3-cyclobuten-1,2-dione (7 mg, 41 μmol) and Et$_3$N (4 mg, 41 μmol) were added. After 3 h the mixture was concentrated. The residue was chromatographed on Sep-Pak (C-18) in water-MeOH (9:1 −7:3) to give 19 (26.8 mg, 84%), $[\alpha]_D$+50.7° (c 0.14; H$_2$O). $^1$H-NMR δ 4.96 (d, 2H, J$_{1",2"}$=8.9 Hz, H-1"), 4.9–4.8 (under HOD, 2H, CH2CH3), 4.52 (m, 4 lines, 2H, H-1"), 4.38 (m, 2H, H-1), 4.34 (broad t, 2H, J$_{5",6"A}$-J$_{5",6"B}$=6.1 Hz, H-5"), 4.25–4.16 (m, 4H), 4.07–4.00 (m, 8H), 3.94–3.55 (m) 3.57 (s, 6H, OMe), 3.49 (t, 2H, J=6.9 Hz), 3.41 (broad t, 2H, J=8.7 Hz), 3.40–3.28 (m, 4H), 3.10 (t, 2H, $^3$J=6.5 Hz, C(O)NHCH$_2$), 1.62 (m, 2H, CH$_2$CH$_2$NHSQ), 1.45 (t, 3H, $^3$J=7.2 Hz, CH$_2$CH), 1.50–1.30 (m, 12H, CH$_2$). Electrospray ionisation MS: 1561.6253 (Calcd. for C$_{62}$H$_{105}$N$_4$O$_{41}$ 1561.6254).

Example 18

Preparation of Pentameric Trisaccharide Dimer 22

A mixture of 1,2,3,4,6-penta-O-allyl-β-D-glucopyranoside (449 mg, 1.18 mmol) and methyl thioglycolate (2.64 mL, 25 eq.) in MeOH (3 mL) was irradiated with a UV source at 254 nm for 1 h and then concentrated, Chromatography of the residue on silica gel in hexane—ethyl acetate (5:5–4:6) gave 20 (545 mg, 51%). $^1$H-NMR δ 4.12 (d, 1H, J$_{1,2}$=7.8 Hz, H-1), 3.90–3.45 (m, 12H, CH$_2$O, H-6a, H-6b), 3.67 (s, 15H, CH$_3$), 3.17 (s, 10H, CH$_2$CO), 3.17–3.11 (m, 3H, H-3, H-4, H-5), 2.96 (m, 1H, H-2), 2.68–2.63 (m, 10H, CH$_2$S), 1.9–1.75 (m, 10H, CH$_2$CH$_2$S). Calc'd for C$_{36}$H$_{62}$O$_2$S$_5$ (911.19): C, 47.45, H, 6.86, S, 17.60. Found C, 47.32, H, 6.91, S, 17.58.

A solution of 20 (170 mg) in neat ethylene diamine was stirred at 60° C. for 2 days, then concentrated and co-evaporated with water. A portion of the mixture was applied to a Sep-Pak cartridge which was washed with water, then the product was eluted with MeOH to give pentaamine 21. $^1$H-NMR δ 4.43 (d, 1H, J$_{1,2}$=8.9 Hz, H-1), 4.02–3.29 (m, 15H, CH$_2$O, H-3, H-4, H-5, H-6a, H-6b), 3.54 (t, 10H, $^3$J=6.1 Hz, CH$_2$N), 3.34 (s, 10H, CH$_2$CO), 3.14 (t, 10H, CH$_2$CN, 3.19–3.09 (m, 1H, H-2), 2.73–2.66 (m, 10H, CH$_2$S), 1.98–1.85 (m, 25H, CH$_2$CH$_2$S, Ac).

Bridged trisaccharide squaric acid derivative 19 (21 mg) was coupled with pentaamine 21 (1.35 mg) in MeOH (2 mL) in the presence Et$_3$N (~2 mg) overnight. The reaction mixture was separated on an HPLC gel column Superdex 75 (eluent=water) to give the pentameric cluster 22 (9 mg). $^1$H-NMR δ 4.97 (d, 10H, J$_{1",2"}$=3.8 Hz, H-1"), 4.52 (m, 4 lines, 10H, H-1'), 4.37 (m, 10H, H-1), 4.35 (t, 10H, J$_{5",6'a}$-J$_{5",6"b}$=6.4 Hz, H-1"), 3.1 (m, 10H, CH$_2$NHC(O)), 2.63–2.59 (m, 10H, CH$_2$S), 1.84 (broad s, 10H, CH$_2$CH$_2$S), 1.63 (broad s, 10H, CH$_2$CH$_2$NH), 1.48 (broad s, 10H, CH$_2$), 1.32 (broad s, 40H, CH$_2$).

Example 19

In Vitro Evaluation

General Method

The bioassay of verotoxin inhibitors are performed in two closely related protocols. Bacterial extracts containing the verotoxin, either verotoxin I or II, or mixtures of both toxin I and II are incubated with inhibitors and added to Mammalian kidney cells (African Green Monkey kidney cells). These cells express the receptor for VTI and VTII and in the absence of inhibitor they bind verotoxin and are killed. Killed cells no longer adhere to the plate and are washed off. Giemsa stain is taken up by the remaining viable cells and the absorbance at 620 nm is a measure of the number of viable cells. The number of viable cells will increase with the efficacy of the inhibitor.

Materials and Methods Bacterial strains. The *E. coli* strains, 0157:H- (E32511), which produces SLT II/SLT IIc (Schmitt, et al., "Two copies of Shiga-like toxin II-related genes common in enterohemorrhagic *Escherichia coli* strains are responsible for the antigenic heterogeneity of the 0 157:H- strain E3251 1," *Infect.Immun.* 59:1065–1073 (1991)) and 026:H11, (H19) which produces SLT I only, were obtained from Dr. S. M. Scotland, Division of Enteric Pathogens, Central Public Health Laboratory, London, U.K. *E. coli* strain C600/933W, producing SLT II only, was provided by Dr. J. L. Brunton, Samuel Lunenfeld Research Institute, Mount Sinai Hospital, Toronto, Ontario.

Tissue culture cells. Vero cells (ATCC CCL 81, American Type Culture Collection, Rockville, Md.) were maintained at 37° C. in an atmosphere of 5% $CO_2$ in minimal essential medium with Earl's salts (MEM, Gibco BRL, Gaithersburg, MD) supplemented with 3% fetal bovine serum (FBS, Gibco BRL). Confluent Vero cell monolayers were disrupted using 0.25% tissue culture grade trypsin (Gibco BRL) and approximately 105 cells in 200 mL of FBS-supplemented MEM were added to each well in 96 well microtiter plates. The microtiter plates were then incubated overnight at 37° C. in 5% $CO_2$.

Preparation of bacterial extracts (toxins). Bacteria were grown overnight at 37° C. on tryptic soy broth (Difco, Detroit, Mich.) agar plates. The polymyxin extraction procedure involved suspending the bacteria in 1 mL of 0.1 M sodium phosphate buffered (pH 7.2) physiological saline (PBS) containing 0.1 mg of polymyxin B sulfate (Sigma Chemical Co. St. Louis, Mo.) as described previously (Karmali, et al., "Sensitive method for detecting low numbers of verotoxin-producing Escherichia coli in mixed cultures by use of colony sweeps and polymyxin extraction of verotoxin," *J.Clin.Microbiol.* 22:614–619 (1985)). After incubating the mixtures at 37° C. for 30 min, the extracts were centrifuged for 10 min in a Eppendorf (Fisher Scientific) model 5413 table top centrifuge. The resulting supernatant solutions were then filter sterilized through Millipore (Millipore Corp., Bedford, Mass.) Millex-GV 0.22 mm filter units.

Vero Cytotoxicity Neutralization Assays

In essence the difference between protocols I and II involves the period for which vero cells are exposed to toxin. Protocol I removes toxin after a 1 hour incubation and cells are then left to grow for 72 hours. Protocol II co-incubates verotoxin, inhibitor and vero cells for the full 72 hour period and assays viability immediately assayed viable cells.

Protocol I (Also Sometimes Called Antibody Protocol)

According to protocol I, the *E. coli* polymyxin extracts were diluted 10 times into unsupplemented MEM and dispensed into 96 well microtiter mixing plates, 180 mL per well, containing no Vero cells. Twenty mL of each inhibitor, dissolved in unsupplemented MEM, was then added to the appropriate wells in these microtiter mixing plates. The FBS-supplemented MEM was discarded from the microtiter plates, prepared as described above, containing the Vero cell monolayers. The inhibitor-extract samples were then immediately transferred from the 96 well mixing plates into the emptied wells in the Vero cell microtiter plates. Diluted bacterial extracts to which no inhibitors were added served as controls. These Vero cell microtiter plates were incubated at 37° C. for 1 h and the medium in each well was then removed using a multichannel automatic pipetor. Each of the emptied wells were carefully washed with 200 mL of fresh FBS-supplemented MEM. This wash solution was discarded and replaced with 200 mL of fresh FBS-supplemented MEM and the microtiter plates were incubated for 72 h at 37° C.

The growth medium was then aspirated from each of the wells in the 96 well microtiter plates and Vero cells which remained viable were fixed to the plastic with 95% methanol and stained with Giemsa stain (Fisher). The results were recorded using a microtiter plate reader set at a wavelength of 620 nm as described previously (2). The resulting absorbance data were plotted versus inhibitor concentration. Individual experiments were always performed in duplicate and, unless otherwise indicated, repeated at least two times.

Protocol II (Also Called Incubation Protocol)

Inhibitors were mixed with bacterial extracts in FBS-supplemented MEM and added to the Vero cell microtiter plates as described above. These plates were then incubated for 72 h at 37° C.

The growth medium was then aspirated from each of the wells in the 96 well microtiter plates and Vero cells which remained viable were fixed to the plastic with 95% methanol and stained with Giemsa stain (Fisher). The results were recorded using a microtiter plate reader set at a wavelength of 620 nm as described previously (Samuel, J.E., et al., "Comparison of the glycolipid receptor specificities of Shiga-like toxin type II and Shiga-like toxin type II variants," *Infect.Immun.* 58:611–618 (1990)). The resulting absorbance data were plotted versus inhibitor concentration. Individual experiments were always performed in duplicate and, unless otherwise indicated, repeated at least two times.

Evaluated Compounds. The compounds tested include a bridged Pk dimer and a conjugate of Pk with bovine serum albumin (BSA). Toxins produced by various strains of *E coli* were evaluated in this study. The results are shown in FIGS. 3a–j.

Results. The data demonstrate that at all concentrations, and with all of the toxins tested, the bridged Pk dimers are more effective than a Pk-BSA conjugate at inhibiting cell lysis caused by the SLT.

Example 20

Comparison of the efficacy of Pk trisaccharides, bridged Pk trisaccharide dimers and multivalent bridged Pk trisaccharides The ability of bridged dimers and trimers of di- and tri-saccharides to bind toxins was compared with that of the corresponding di- and tri-saccharides. Bridges between two di-saccharides, a mixture of a di-saccharide and a tri-saccharide, and two tri-saccharides were formed by reacting a hydroxy group on the Pk disaccharides or trisaccharides with p-nitrophenyl carbonate, and forming two urea linkages (hence forming a dimer) by reaction with a diamine.

An ELISA assay was performed comparing the bridged dimers to a Pk tri-saccharide, and the $IC_{50}$ values for each of the compounds was obtained, the results of which are shown in FIG. 4.

Verotoxin I dissolved in phosphate buffered saline (PBS) (2.5 micrograms per mL) was coated on 96 well ELISA plates overnight at 4 degrees. The plate was washed 4 times with PBS containing Tween 20 (0.05% v/v). The plate was blocked with milk (Difco) 2.5% in PBS for 1 hr. The plate was then washed twice with PBS containing Tween 20 (PBST).

A Pk trisaccharide conjugated to BSA and biotinylated (10 micrograms per mL) was mixed with inhibitor at concentrations in the range 0.1 nanomolar to 10 millimolar. The mixture was added to the coated microtitre plate and incubated at room temperature for 18 hr. The plate was washed 4 times with PBST and streptavidin horseradish peroxidase was added and incubated for 1 hr at room temperature. The plate was washed 4 times with PBST and TMB horse radish peroxidase substrate was added and after 2 minutes the color reaction was stopped with 1M phosphoric acid. Absorbance was read at 450 nm and percent inhibition was calculated using wells containing no inhibitor as the reference point.

Figure 4:
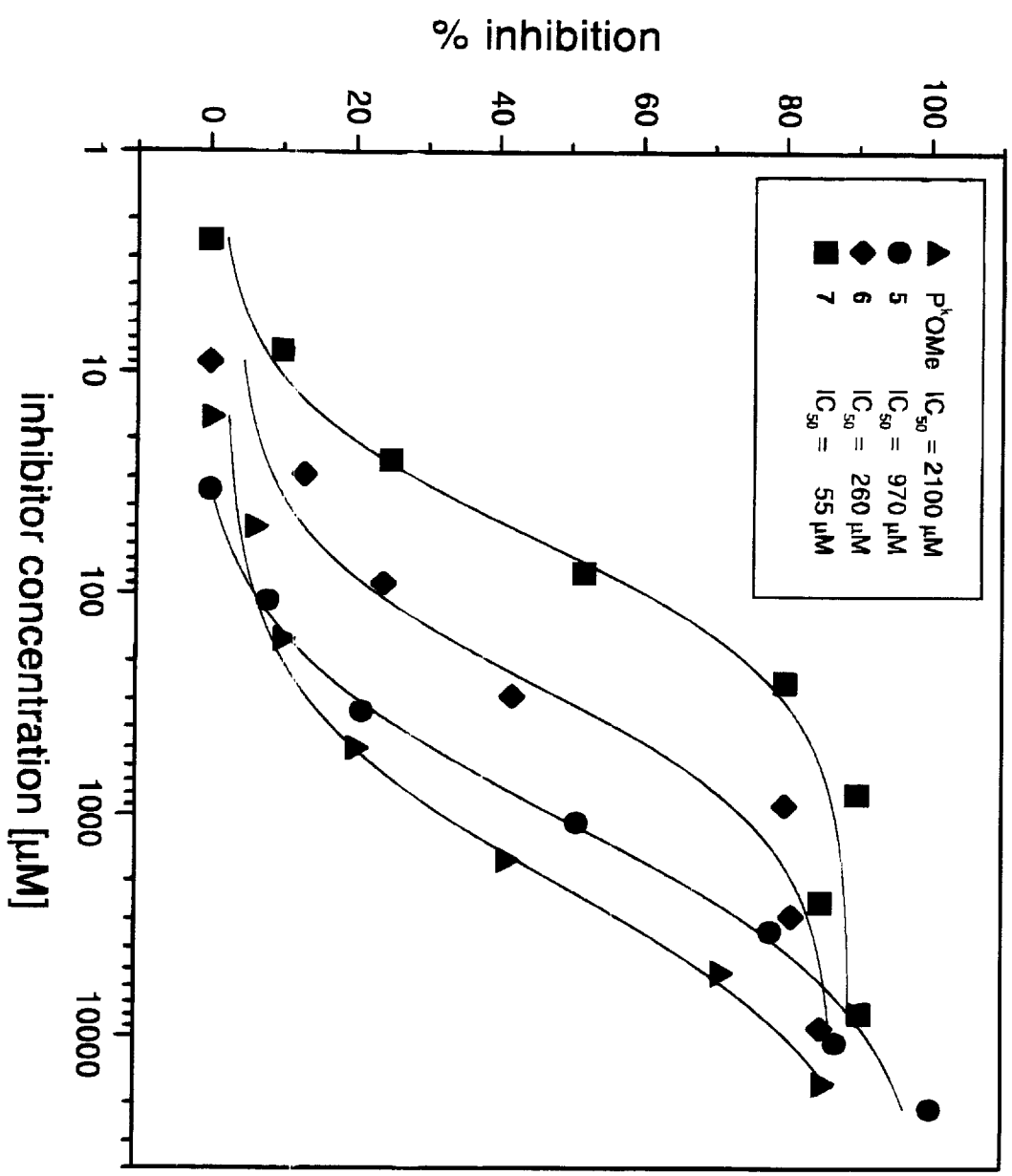
FIG. 4 is a graph comparing the inhibitory power of various bridged Pk disaccharides and trisaccharides with unbridged Pk trisaccharide towards VT-I in an ELISA assay as a function of percent inhibition (%) vs. inhibitor concentration ($\mu$M). Triangles represent Pk trisaccharide. Circles represent a bridged dimer of a Pk disaccharide. Diamonds represent a bridged dimer that includes one Pk disaccharide and one Pk trisaccharide. Squares represent a bridged dimer that includes two Pk trisaccharides. The bridges were formed by reacting a hydroxy group on the Pk disaccharides or trisaccharides with p-nitrophenyl carbonate, and forming two urea linkages (hence forming a dimer) by reaction with a diamine.
Figure 5:
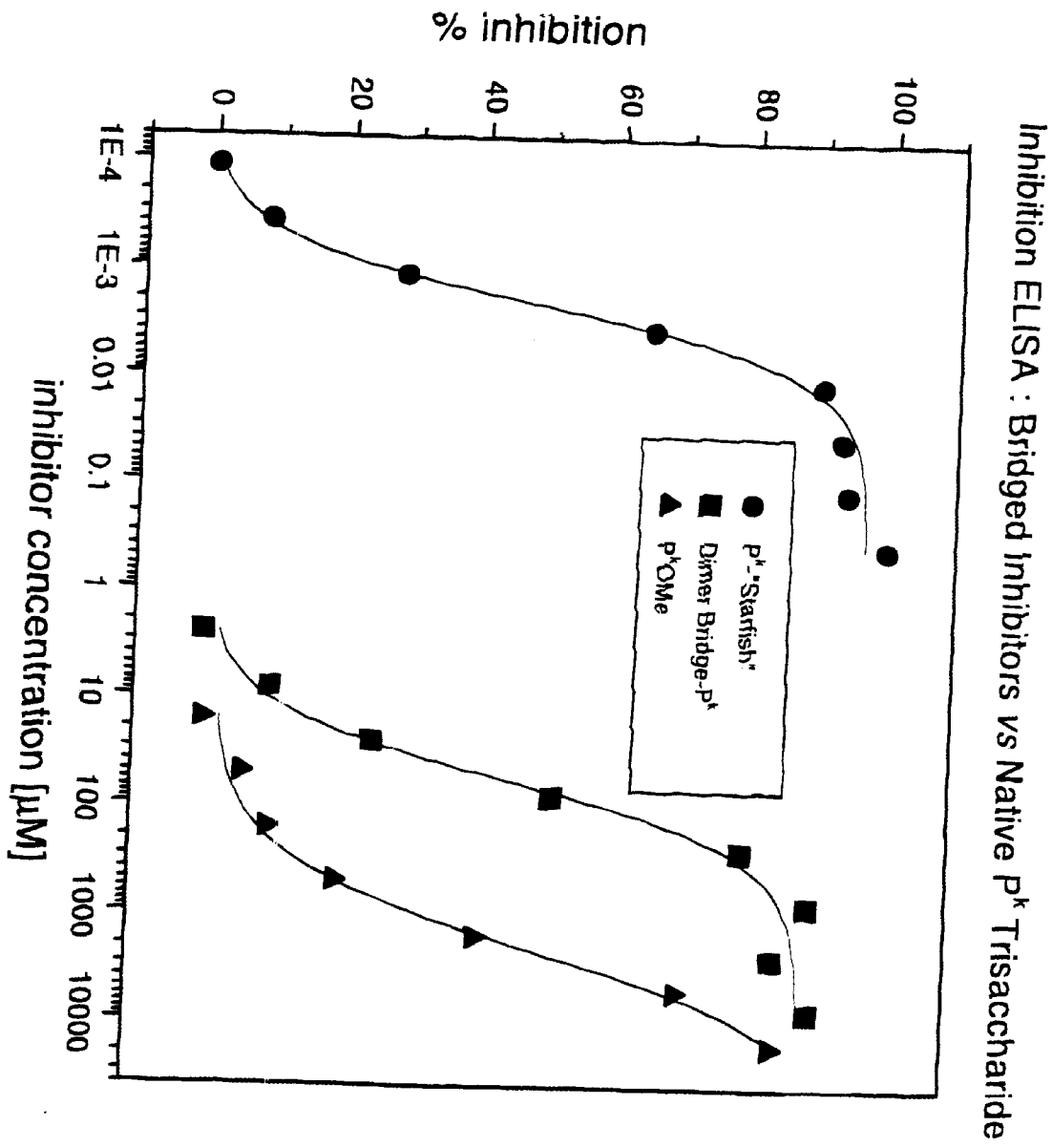
FIG. 5 is a graph comparing the inhibitory power of Compound 22 ("starfish") with a bridged dimer of Pk trisaccharides and with unbridged Pk trisaccharide towards VT-1 in an ELISA assay as a function of percent inhibition (%) vs. inhibitor concentration ($\mu$M). Triangles represent Pk trisaccharide. Squares represent a bridged dimer of a Pk trisaccharide. Circles represent the "starfish" molecule.

As shown in FIG. 4, the $IC_{50}$ for the Pk trisaccharide was 2100 $\mu$M, the bridged dimer of two Pk disaccharides was 970 $\mu$M, the bridged dimer of a Pk disaccharide and a Pk tri-saccharide was 260 $\mu$M, and the bridged dimer of two Pk trisaccharides was 55 $\mu$M. This data demonstrates that the bridged dimers are more active than the monomers. The bridged dimer of two Pk trisaccharides was 38 times higher than the Pk trisaccharide alone, yet only includes twice the number of saccharide moieties. Accordingly, the bridged dimers and trimers are more active than the monomeric di- or trisaccharides, even without being bound to a linker arm, and subsequently bound to a multifunctional core molecule.

However, when the Pk trisaccharide and the bridged dimer of trisaccharides was compared to Compound 22 ("starfish") as disclosed herein, using a similar ELISA, the starfish molecule was about 10,000 times more active than the bridged trisaccharide dimer and about a million times more active than the trisaccharide alone.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

What is claimed is:

1. A compound of the following structure:

MFC-(LA)$_n$-(BM)$_n$ wherein:

MFC is a multifunctional core molecule,

LA is a linker arm,

BM is a bridging molecule which includes two or more di-or tri-saccharides, and which can optionally include large oligosaccharides, n is, independently, between 3 and 20, the di- or tri-saccharide moiety are optionally linked to between one and eight additional saccharide moieties, and include an individual saccharide moiety selected from the group consisting of $\alpha$Gal(1→4)$\beta$Gal, $\alpha$Gal(1→4)$\beta$Gal(1→4)$\beta$GlcNAc, and $\alpha$Gal(1→4)$\beta$Gal(1→4)$\beta$Glc, the bridging moieties are bound to at least one linker arm, the linker arms are, independently, C6-20 straight, branched or cyclic alkanes, in which one or more of the carbons may optionally be replaced with an O, S, or amine, and the linker arms can optionally be functionalized at one or more positions with a functional group selected from the group consisting of aryl, substituted aryl, heteroaryl, substituted heteroaryl, heterocyclic and substituted heterocyclic, and pharmaceutically acceptable salts thereof.

2. The compound of claim 1 wherein the multifunctional compound is selected from the group consisting of monosaccharides, oligosaccharides, aldaric acids, amino acids, peptides, acrylamides, cyclodextrins, phthalocyanins and polyhydroxy alkanes.

3. The compound of claim 1 wherein at least one of the linker arms is selected from the group consisting of polymethylene, aryl groups, aralkyl groups alkaryl groups, alkylcycloalkanes, polyalkylene glycols, alkyl diamines, alkyl thio amines, and alkyl dithiols.

4. The compound of claim 1 wherein the bridging moieties include at least one functional group selected from the group consisting of carbamoyl, amide, carboxylic acid, hydroxy, thiol, amine, aldehyde, ketone, thioacid, thioester, thiourea, sulfonic acid, and phosphoric acid.

5. The compound of claim 1 wherein at least one of the saccharide moieties is a dimer or trimer including a saccharide selected from the group consisting of $\alpha$Gal(1→4)$\beta$Gal, $\alpha$Gal(1→4)$\beta$Gal(1→4)$\beta$GlcNAc and $\alpha$Gal(1→4)$\beta$Gal(1→4)$\beta$Glc., wherein the aglycon of the terminal reducing saccharide is alkyl, aryl, aralkyl, alkaryl, allyl or the corresponding thio analogues.

6. The compound of claim 1 wherein the number of linker arms is between 3 and 20.

7. The compound of claim 1, further comprising a pharmaceutically acceptable carrier for administration to a patient.

8. A method for treating an enteric infection mediated by an SLT in a subject comprising administering to the subject in need of such treatment an amount sufficient to treat the enteric infection of a composition comprising a compound of claim 1.

9. The method of claim 8 wherein the compound includes the oligosaccharide sequence $\alpha$Gal(1→4)$\beta$Gal.

10. The method of claim 8 wherein the compound includes the oligosaccharide sequence $\alpha$Gal(1→4)$\beta$Gal(1→4)$\beta$GlcNAc.

11. The method of claim 8 wherein the compound includes the oligosaccharide sequence $\alpha$Gal(1→4)$\beta$Gal(1→4)$\beta$Glc.

12. The method of claim 8 wherein the linker arm comprises from 6 to 10 carbon atoms.

13. The method of claim 8 wherein the linker arm is —(CH$_2$)$_8$C(O)—.

14. The method of claim 8 wherein the compound is covalently bound to or adsorbed onto a solid inert affinity support.

15. The method of claim 8 wherein the pharmaceutical composition is administered to the patient prior to organ involvement other than intestinal involvement.

16. The method of claim 8 wherein the compound is administered orally.

17. The method of claim 8 wherein the compound is administered via injection.

18. A method for diagnosing enteric infections mediated by SLTs in a patient comprising obtaining a biological sample from the patient and assaying for the presence of the SLT in a binding assay which uses a compound according to claim 1 to bind to the SLT.

19. The method of claim 18 wherein the compound includes a label selected from the group consisting of radiolabels, fluorescent tags, biotin, streptavidin, and enzymes which enable the compound to be detected after it has been bound to the SLT.

* * * * *